United States Patent
Onouchi

(10) Patent No.: US 10,884,143 B2
(45) Date of Patent: Jan. 5, 2021

(54) RADIATION IMAGING APPARATUS

(71) Applicant: Hitachi, Ltd., Tokyo (JP)

(72) Inventor: Masafumi Onouchi, Tokyo (JP)

(73) Assignee: Hitachi, Ltd., Tokyo (JP)

(*) Notice: Subject to any disclaimer, the term of this patent is extended or adjusted under 35 U.S.C. 154(b) by 41 days.

(21) Appl. No.: 16/479,276

(22) PCT Filed: Feb. 19, 2018

(86) PCT No.: PCT/JP2018/005791
§ 371 (c)(1),
(2) Date: Jul. 19, 2019

(87) PCT Pub. No.: WO2018/163782
PCT Pub. Date: Sep. 13, 2018

(65) Prior Publication Data
US 2019/0383954 A1 Dec. 19, 2019

(30) Foreign Application Priority Data
Mar. 7, 2017 (JP) ................................. 2017-042865

(51) Int. Cl.
*G01T 1/24* (2006.01)
*A61B 6/03* (2006.01)
*G01T 1/161* (2006.01)

(52) U.S. Cl.
CPC .............. *G01T 1/24* (2013.01); *A61B 6/03* (2013.01); *G01T 1/161* (2013.01); *G01T 1/244* (2013.01)

(58) Field of Classification Search
CPC .......... G01T 1/24; G01T 1/161; G01T 1/244; A61B 6/03; A61B 6/585; A61B 6/4241; A61B 6/032

(Continued)

(56) References Cited

U.S. PATENT DOCUMENTS 8,476,594 B2 * 7/2013 Frach .................... G01T 1/2985
250/363.03
9,113,542 B2   8/2015 Hackenschmied et al.
(Continued)

FOREIGN PATENT DOCUMENTS

| JP | 2008123767 A | 5/2008 |
| JP | 2012501443 A | 1/2012 |
| WO | 2016046014 A1 | 3/2016 |

OTHER PUBLICATIONS

International Preliminary Report on Patentability, dated Sep. 19, 2019, which issued during the prosecution of International Application No. PCT/JP2018/005791, which corresponds to the present application.

*Primary Examiner* — David P Porta
*Assistant Examiner* — Gisselle M Gutierrez
(74) *Attorney, Agent, or Firm* — Baker Botts L.L.P.

(57) ABSTRACT

Provided is a radiographic imaging apparatus including a photon-counting detector that prevents variation in count rate performance by using self-heating of a photon-counting circuit, and improves accuracy in detecting photons. The photon-counting detector is provided with a semiconductor layer configured to generate electrical charge upon receipt of photons of radiation, a photon-counting circuit configured to read current values from pixel electrodes formed on one of the semiconductor surfaces, and a heat amount compensator configured to control an amount of heat of the photon-counting circuit according to a count rate of the photon-counting circuit. The heat amount compensator is activated when the count rate is low so that the amount of heat delivered from the photon-counting circuit when the count is low becomes nearly equal to the amount of heat delivered from the photon-counting circuit when the count rate is high.

16 Claims, 17 Drawing Sheets

(58) Field of Classification Search
USPC .................................................. 250/370.09
See application file for complete search history.

(56) References Cited

U.S. PATENT DOCUMENTS

| | | | |
|---|---|---|---|
| 2009/0128216 A1 | 5/2009 | Rao et al. | |
| 2009/0132789 A1* | 5/2009 | Rao | G06G 7/18 |
| | | | 712/36 |
| 2011/0291017 A1* | 12/2011 | Frach | G01T 1/244 |
| | | | 250/366 |
| 2014/0211910 A1 | 7/2014 | Subramanian et al. | |
| 2015/0076357 A1* | 3/2015 | Frach | G01T 1/2018 |
| | | | 250/370.08 |
| 2017/0219426 A1* | 8/2017 | Pacala | G01S 7/497 |
| 2018/0209841 A1* | 7/2018 | Pacala | G01S 17/42 |
| 2018/0292551 A1* | 10/2018 | Danielsson | G01T 1/2985 |
| 2019/0137636 A1* | 5/2019 | Frach | G01T 7/005 |

* cited by examiner

COUT30  COUT31  COUT32  COUT33

FIG. 7A

| PHOTON COUNT RATE OF COUT1 | HEATING VALUE OF HEATING BLOCK 251-A | HEATING VALUE OF HEATING BLOCK 251-B | HEATING VALUE OF HEATING BLOCK 251-C | HEATING VALUE OF HEATING BLOCK 251-D |
|---|---|---|---|---|
| $R_{100}$ | $P_{300}$ | $P_{310}$ | $P_{320}$ | $P_{330}$ |
| $R_{101}$ | $P_{301}$ | $P_{311}$ | $P_{321}$ | $P_{331}$ |
| ... | ... | ... | ... | ... |
| $R_{10J}$ | $P_{30J}$ | $P_{31J}$ | $P_{32J}$ | $P_{33J}$ |

FIG. 7B

| PHOTON COUNT RATE OF COUT2 | HEATING VALUE OF HEATING BLOCK 251-E | HEATING VALUE OF HEATING BLOCK 251-F |
|---|---|---|
| $R_{210}$ | $P_{340}$ | $P_{350}$ |
| $R_{211}$ | $P_{341}$ | $P_{351}$ |
| ... | ... | ... |
| $R_{21J}$ | $P_{34J}$ | $P_{35J}$ |

HEATING-VALUE CONTROL REGION

RADIATION IMAGING APPARATUS

CROSS-REFERENCE TO RELATED APPLICATIONS

This application is a national phase claiming the benefit of and priority to International Patent Application No. PCT/JP2018/005791, entitled "RADIATION IMAGING APPARATUS", filed Feb. 19, 2018, which claims priority to Japanese Patent Application No. 2017-042865, filed Mar. 7, 2017 which are hereby incorporated by reference in their entireties.

TECHNICAL FIELD

The present invention relates to a radiation imaging apparatus (radiographic imaging apparatus) incorporating a photon-counting detector. More particularly, the present invention relates to a technique for avoiding degradation of circuit performance due to variation in amount of heat within a circuit that reads electrical charge used for detecting photons generated in a semiconductor cell of the photon-counting detector.

BACKGROUND ART

In recent years, photon-counting CT (Computed Tomography) devices incorporating a detector that employs a photon-counting system (photon-counting detector) have been developed in various institutions. Unlike charge-integrating type detectors employed in conventional CT devices, the photon-counting detector is capable of counting individual radiation photons that enter detector elements. With this configuration, this photon-counting detector features that energy for each incident radiation photon can be measured and much more information can be obtained relative to the conventional CT devices.

The detector element of the photon-counting detector is provided with a semiconductor layer such as cadmium zinc telluride (CZT) and cadmium telluride (CdTe). Every time the radiation photon enters the semiconductor layer, a charge in association with the radiation photon is generated therein. A photon-counting circuit connected to an electrode formed in the semiconductor layer reads thus generated charge.

This type of photon-counting detector has a problem that count rate performance may vary due to temperature change in components related to photon counting. For example, entry of radiation photons generates current in the semiconductor layer, causing the temperature change in the semiconductor layer, resulting in change of characteristics of the semiconductor layer, and this is considered to be one of the causes of the variation in the count rate performance. As a method for avoiding such change of the characteristics of the semiconductor layer, the Patent Document 1 discloses a technique for providing an additional radiation source to a semiconductor layer, on the basis of an incident photon rate.

PRIOR ART DOCUMENT

Patent Document

Patent Document 1
U.S. Pat. No. 9,113,542 DESCRIPTION

DISCLOSURE OF THE INVENTION

Problems to be Solved by the Invention

In recent years, an operating rate of a counting circuit in a photon-counting CT apparatus has been enhanced, so as to improve a count rate in counting radiation photons. In the counting circuit, a photon count rate (the number of photons counted per unit time) has positive correlation with power consumption, in general. Therefore, the lower is the photon count rate, the lower is the power consumption, and the higher is the photon count rate, the higher is the power consumption. When improvement of the count rate increases the maximum power consumption of the counting circuit, this may also increase the amount of fluctuation of the power consumption along therewith. In other words, if it is attempted to achieve a high count rate, this may cause increase of an amount of temperature change in the counting circuit. Accordingly, maintaining the photon count rate performance across a wide range of the photon count rates may become difficult. In order to maintain stable performance of the photon count rate in association with the wide range of the count rates in the photon-counting CT apparatus, the need for preventing temperature change caused by heat generation in the counting circuit is now more intensified than preventing the temperature change caused by heat generation in a semiconductor layer.

The technique described in the patent document 1 is to prevent temperature change in the semiconductor layer. Though this technique is applied to a photon-counting detector implementing a high count rate, it is difficult to prevent variation in the count rate performance of the counting circuit itself.

The present invention has been made in view of the situation as described above, and an object of the present invention is to prevent variation in performance of the counting circuit, caused by amount of heat change in the counting circuit due to an incidence rate of radiation photons, and to improve detection accuracy.

Means for Solving the Problems

In order to solve the above problems, the radiographic imaging apparatus of the present invention is provided with a radiation source, and a photon-counting detector configured to detect radiation emitted from the radiation source and to output electrical signals in association with the number of photons of the radiation, and further provided with a photon-counting circuit configured to count the number of photons, and a heat amount compensator configured to control an amount of heat of the photon-counting circuit according to detection of the number of photons, so as to provide the amount of heat independent of the number of counted photons.

Advantages of the Invention

According to the present invention, when current pulse signals generated in the semiconductor layer are counted at high count rate, variation in the count rate performance of the counting circuit can be prevented and this allows enhancement of detection accuracy.

BRIEF DESCRIPTION OF THE DRAWINGS

FIGS. 7A and 7B show table examples used for the heat amount control according to the first embodiment;

BEST MODE FOR CARRYING OUT THE INVENTION

There will now be described embodiments of the present invention with reference to the accompanying drawings. The present invention directed to a radiographic imaging apparatus is applied to an apparatus provided with a radiation source and a photon-counting detector. In the present embodiment, there will be described an example where radiation is in the form of rays and an imager is a CT apparatus.

Figure 1:
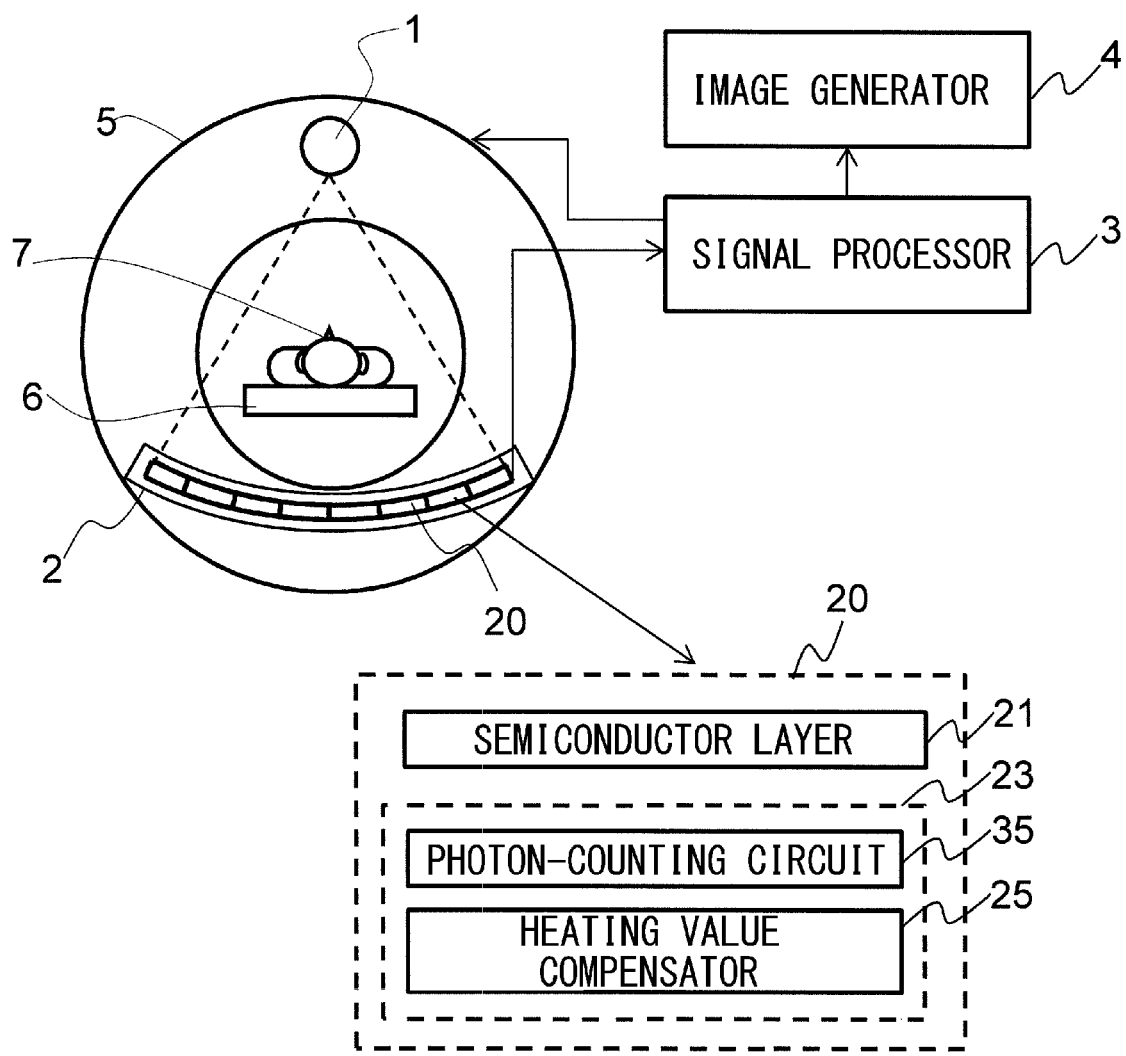
FIG. 1 illustrates an overall configuration of an X-ray CT apparatus to which the present invention is applied.

As shown in FIG. 1, the X-ray CT apparatus of the present embodiment comprises an X-ray source 1 configured to apply X rays, an X-ray detector 2 including a plurality of detector elements in a two-dimensional array for detecting X rays, a signal processor 3 configured to perform processing such as correction on signals detected by the detector elements with controlling the apparatus, and an image generator 4 configured to generate an image of a subject 7 by using the corrected signals. The X-ray source 1 and the X-ray detector 2 are fixed on a rotary plate 5, being opposed to each other, and configured in a manner that they are relatively rotatable about the subject 7 laid on a table 6. The X-ray source 1 and the X-ray detector 2 including the rotary plate 5 may be referred to as a scanner.

The detector elements constituting the X-ray detector 2 are photon-counting detectors, each provided with a semiconductor layer 21 configured to output electrical charge corresponding to photons of X rays being entered, and a photon-counting circuit (hereinafter, simply referred to as a counting circuit) 35 configured to count the electrical charge outputted from the semiconductor layer 21 and to output a count signal. In addition, the counting circuit 35 is provided with a heat amount compensator 25 configured to maintain an amount of heat of the counting circuit 35 in a manner that maintains the amount of heat nearly constant irrespective of the photon count rate. The counting circuit 35 and the heat amount compensator 25 may be integrated on an identical chip 23, or they may be configured as separated components. An example of the configuration on an identical chip will be described in the following embodiments, from the first to the third embodiments, and an example of the configuration of the separated components will be described in the fourth embodiment. The semiconductor layer 21 is similar to a conventional semiconductor layer of cadmium-zinc-telluride (CZT), cadmium telluride (CdTe), or a similar material. Specific configurations of the counting circuit 35 and the heat amount compensator 25 will be described below.

An imaging operation of the X-ray CT apparatus having such configuration as described above may be similar to a conventional X-ray CT apparatus. That is, the X-ray source 1 is placed being opposed to the X-ray detector 2, relatively rotating around the subject 7, emitting X rays from the X-ray source 1, and the X-ray detector 2 detects the X rays passing through the subject 7. The signal processor 3 applies processing such as correction as needed, to the count signal outputted from the chip 23 of the X-ray detector 2, and then the image generator 4 generates a tomographic image (CT image) of the subject.

The amount of X rays passing through the subject 7, in other words, the number of photons counted in the counting circuit 35 (photon count rate), may be different depending on the position of the X-ray detector 2, and also depending on an angle of rotation. In response to such variation in the photon count rate, the circuit power consumption of the counting circuit 35 also varies, causing a change of amount of heat that affects count rate performance of the counting circuit 35. The heat amount compensator 25 is activated in a manner that maintains the amount of heat of the counting circuit 35 nearly constant.

Figure 2:
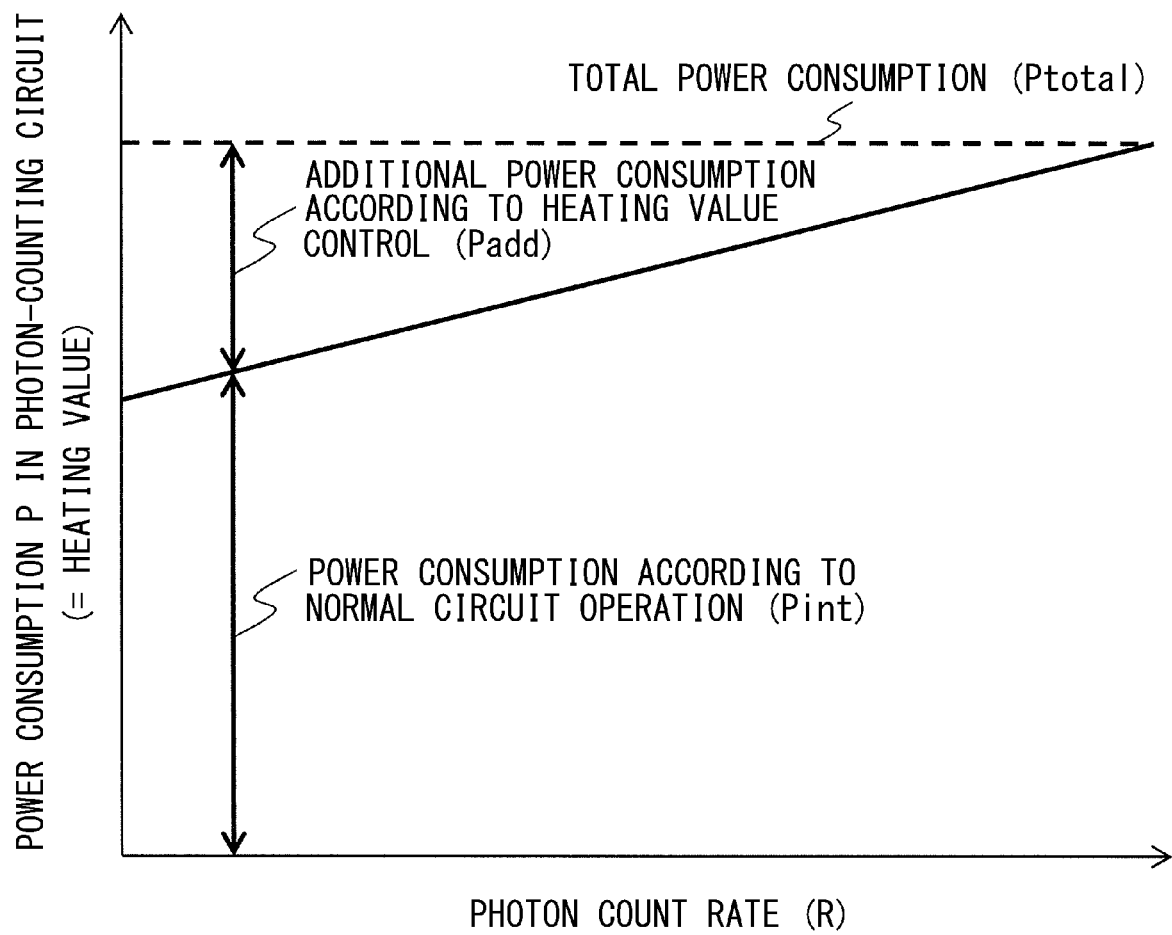
FIG. 2 is a graph showing an overview of heat amount control according to an embodiment.

With reference to FIG. 2, there will now be described a function of the heat amount compensator 25. FIG. 2 shows a relation between the photon count rate (R) and the power consumption P of the counting circuit. As indicated by the solid line in FIG. 2, the circuit power consumption (Pint) of the counting circuit increases in accordance with increase of the photon count rate (R) under normal circumstances. In this normal circuit operation, the count rate performance may vary according to variation in generated power consumption (Pint). The heat amount compensator 25 operates to carry out additional power consumption (Padd) in a manner that cancels the variation in the power consumption (Pint) during the normal circuit operation. With this configuration, as indicated by the dotted line in FIG. 2, total power consumption (Ptotal) for the photon-counting circuit can be kept constant. Accordingly, this allows an operating temperature of the counting circuit 35 to be constant, thereby maintaining the count rate performance to be constant.

The heat amount compensator 25 may operate in a manner that obtains a predicted value of the photon count rate in advance based on preliminary counting, and perform control according to this predicted value or feedback control using the number of photons being the output from the counting circuit 35. In general, imaging cycle in the X-ray CT apparatus is equal to 1 msec or less, and it is shorter than a time constant of temperature change of a structure containing the counting circuit 35 and the heat amount compensator 25. Therefore, compensating for the amount of heat at every imaging cycle allows an operating temperature around the counting circuit 35 and the heat amount compensator 25 to be kept constant.

In FIG. 2, the power consumption (Pint) according to the normal circuit operation and the additional power consumption (Padd) are simply expressed as linear functions with the incident photon rate (photon count rate) (R), but in actual, they may not form clear linearity. FIG. 2 also illustrates that the total power consumption (Ptotal) is constant, but in actual control, there may be some variations to the extent that they do not interfere with the count rate performance.

An effect of the present embodiment will be described using a relation with "dead time (τ)" that corresponds to the time from incidence of photons to completion of the circuit operation for counting the photons. In general, the counting circuit needs to reserve the circuit operation time for counting photons, and the time from incidence of photons to the completion of the circuit operation for counting the photons, corresponds to the "dead time (τ)". In this situation, the relationship of the following equation 1 is given, where an observed count rate is n, and a true count rate is r.

[Equation 1]

$$n = \frac{r}{1 + r\tau} \quad (1)$$

In order to obtain the true count rate r from the observed count rate n, by using this equation 1, it is necessary to know the dead time τ accurately. Here, the dead time τ varies according to the operating temperature of the circuit. The activated state of the counting circuit varies in response to the photon incidence rate, and the temperature is low at a low incidence rate, whereas the temperature is high at a high incidence rate. Therefore, an error may arise when the count rate at the high incidence rate is corrected by using the value τ obtained at low incidence rate. In the present embodiment, according to the heat amount compensator, the amount of heat of the counting circuit is controlled so that the activated state at low incidence rate could be the same as the activated state at high incidence rate, thereby canceling temperature dependence of the dead time T, and allowing acquisition of the true count rate r accurately.

Next, there will now be described embodiments of specific configuration of the counting circuit 35 and the heat amount compensator 25.

First Embodiment

The present embodiment features that a heating element is employed as the heat amount compensator and the heating element is provided for each of circuit components constituting the counting circuit. With reference to FIG. 3, a radiographic imaging apparatus of the present embodiment will be described. The X-ray CT apparatus as shown in FIG. 1 will be taken as an example.

Figure 3A:
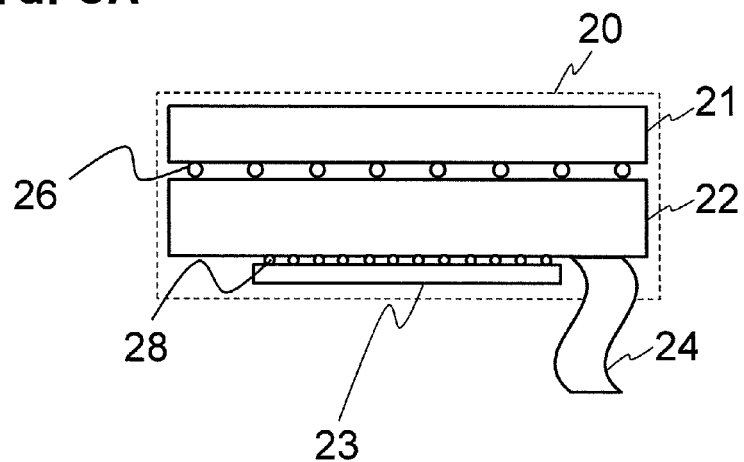
FIG. 3A illustrates a detection module constituting an X-ray detector of an embodiment.

First, a structure of a module 20 constituting the X-ray detector 2 will be described. The X-ray detector 2 as shown in FIG. 1 includes the modules 20 comprising a plurality of detector elements in arc-shaped arrangement. As shown in FIG. 3A, each module is provided with, as primary components, a semiconductor layer 21 for detecting photons, a chip 23 including the counting circuit 35 and the heat amount compensator 25, and a substrate 22 for connecting the semiconductor layer 21 with the chip 23. The substrate 22 is connected to a cable 24 for taking the output of the counting circuit 35 to the outside. The semiconductor layer 21 is electrically connected with the substrate 22 via a connection array 26, and the substrate 22 is electrically connected with the chip 23 via a connection array 28.

Figure 3B:
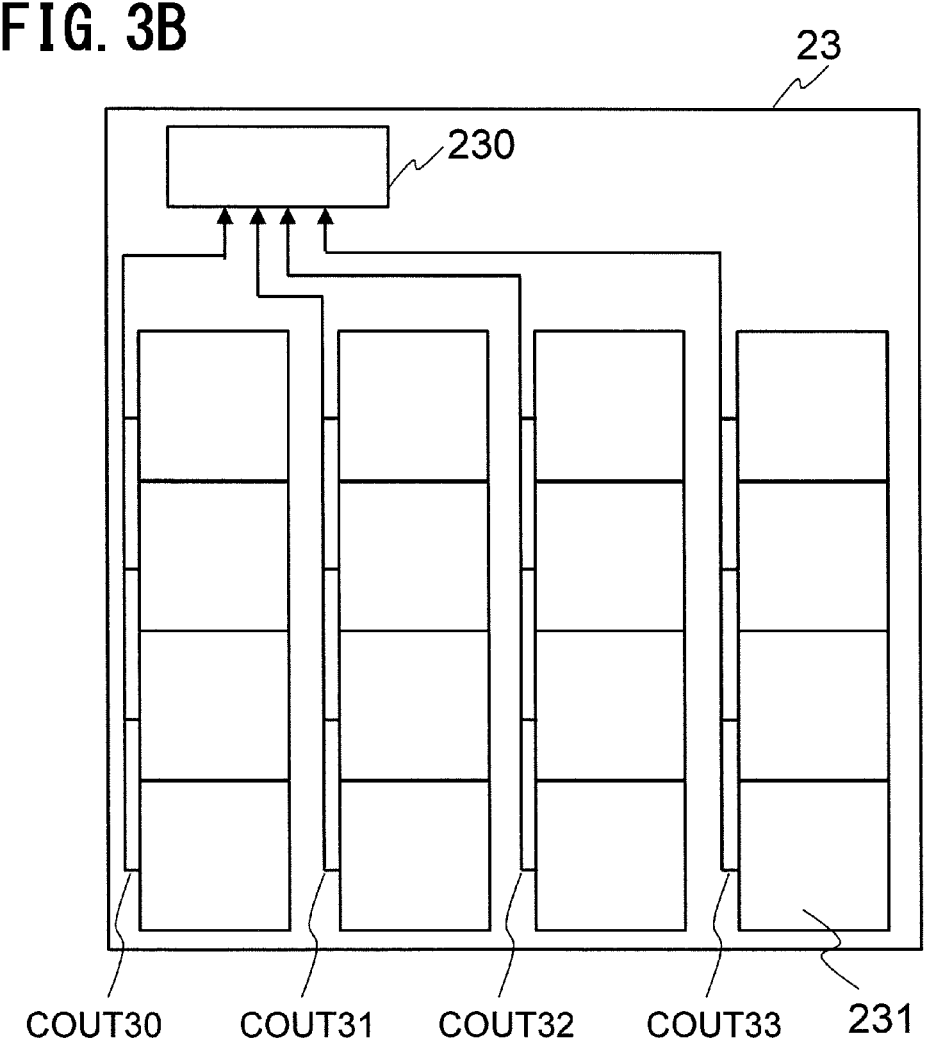
FIG. 3B illustrates a configuration of counting circuits.

The chip 23 is formed as an LSI (large-scale integration) made up of a large number of circuit components, and as shown in FIG. 3B, there are arranged a plurality of photon counting blocks (counting circuits) 231 and an output block 230 for collecting and outputting the results of counting from the photon counting blocks. A photon counting block 231 corresponds to a pixel, and in the illustrated example, the number of pixels are 4×4 for counting the photons entering the semiconductor layer 21 by each of the photon counting blocks, that is, counting pixel by pixel. The output block 230 is notified of the number of photons being counted, at every predetermined time that is notified from a host controller not illustrated. In the figure, signals collected within the chip for outputting the count result pixel by pixel to the host controller, are indicated as COUT30, COUT31, COUT32, and COUT33, respectively.

Figure 4:
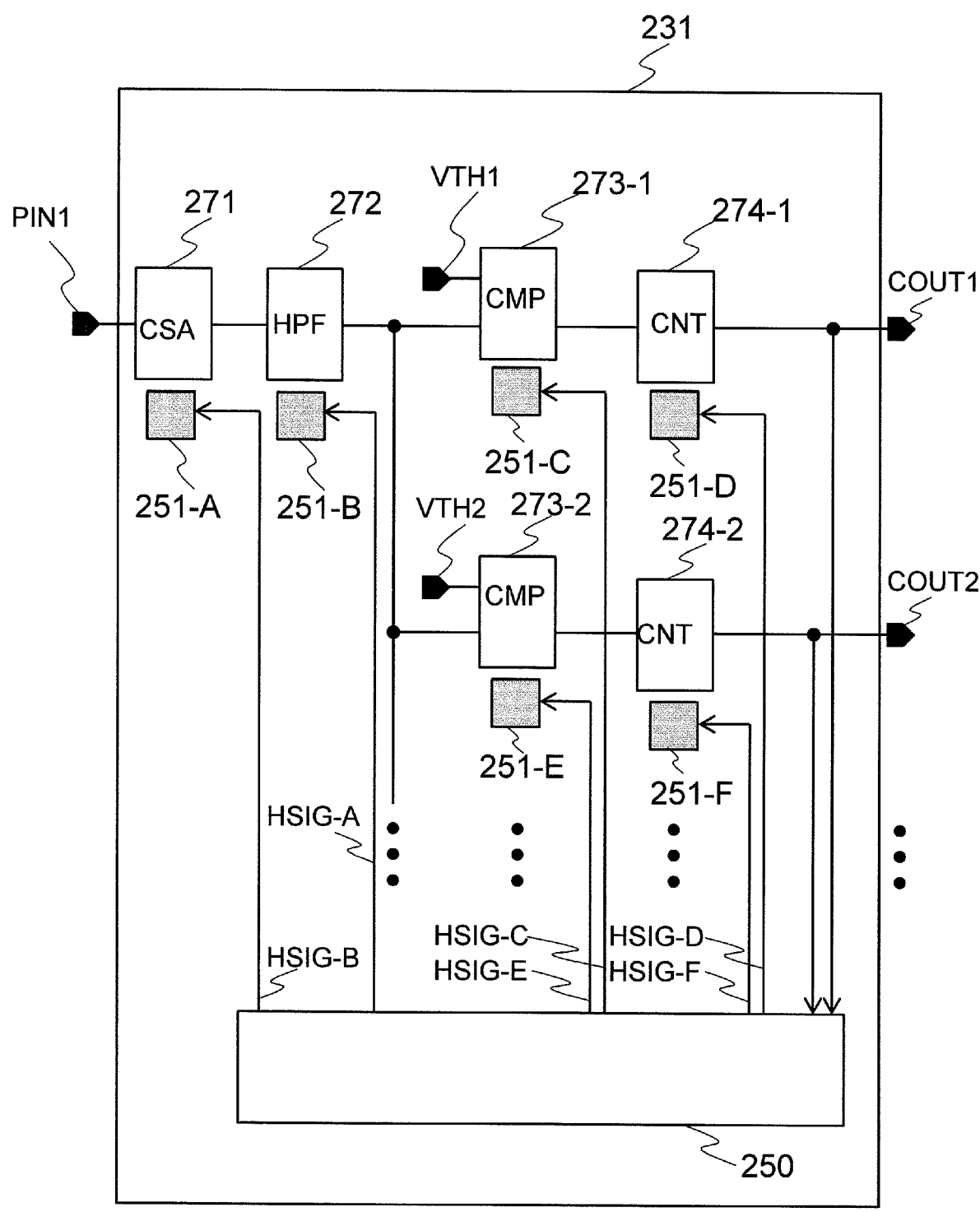
FIG. 4 is a block diagram showing a configuration of a photon-counting circuit relating to a first embodiment.

In the present embodiment, the heat amount compensators 25 are placed within the individual photon counting blocks 231. With reference to FIG. 4, there will be described an internal configuration of the photon counting block 231, and a configuration and layout of the heat amount compensator 25.

As shown in FIG. 4, input pins to the photon counting block 231 are, current input pin PIN1, threshold voltage VTH1, VTH2 ... and output pins from the photon counting block 231 are count value output pins COUT1, COUT2 .... The threshold voltage corresponds to a threshold of X-ray energy, and it is configured so that X rays at a plurality of energy levels are discriminated and detected.

In the photon counting block 231, there are arranged, as circuit components functioning as the counting circuit, a charge amplifier (CSA) 271, a high-pass filter (HPF) 272, voltage comparators (CMP) 273-1, 273-2 ... and counters (CNT) 274-1, 274-2 .... The voltage comparators 273-1, 273-2 ... and the counters 274-1, 274-2 ... are arranged, the number of which corresponds to the number of energy levels being detected, and different threshold voltage is inputted in each voltage comparator. If there is no particular distinction among the multiple voltage comparators or among the multiple counters, descriptions will be provided by using the reference numerals 273 and 274, eliminating the numbers following the hyphen.

The heat amount compensator 25 comprises a plurality of heating blocks 251, and a heating control block 250 for controlling those heating blocks. The heating blocks 251 are arranged in proximity to the individual circuit components (CSA, HPF, CMP, and CNT). If distinctions are made among the individual heating blocks 251, reference symbols from A to F are attached to the end of the reference numeral 251, the reference symbols A to F respectively associated with the control signals HSIG directed to the respective heating blocks 251 from the heating control block 250.

In the configuration as described above, the input (current signal) from the current input pin PIN1 is subjected to shaping as a voltage value via the charge amplifier 271 and the high-pass filter 272, and its peak value is compared with each of threshold VTH1 and others, by using a plurality of voltage comparators 273 and others. The counter 274 counts the number of counts where the peak value after the shaping exceeds each threshold. At this time, the output block 230 (FIG. 3) is notified of the photon counting results COUT1, COUT2 ... in the respective counters of the photon counting block 231, and the heating control block 250 is also notified of the results.

On the basis of the photon counting result, the heating control block 250 makes a notification of amounts of heat of the respective heating blocks 251 according to the signals HSIG-A to HSIG-F, so that the amounts of heat in the photon counting block 231 becomes constant.

Figure 5A:
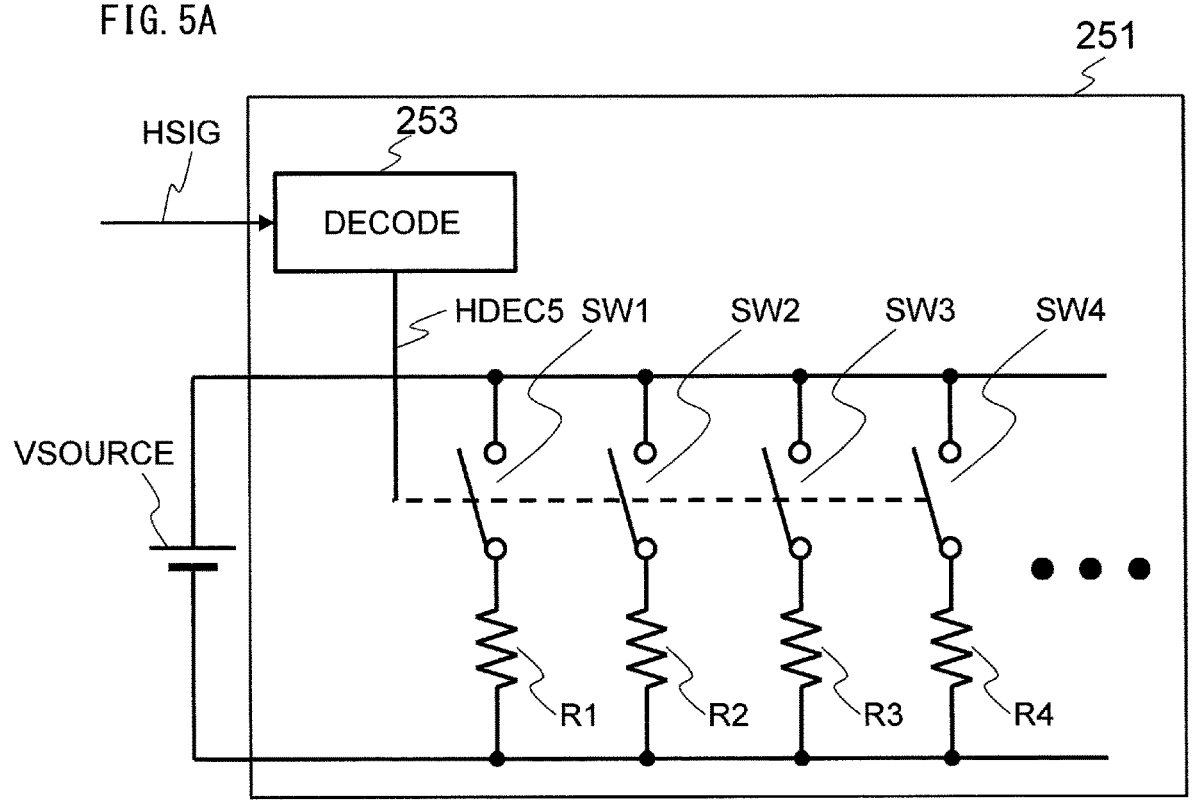
FIG. 5A is a block diagram showing a heat generation circuit relating to the first embodiment.
Figure 5B:
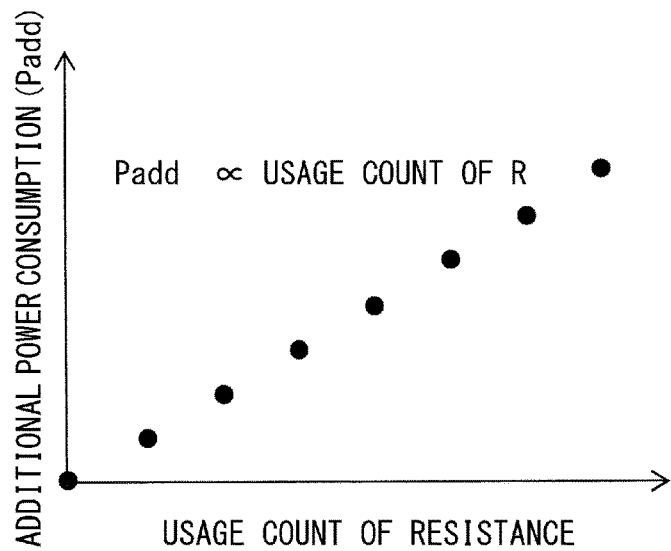
FIG. 5B illustrates the heat amount control of the heat generation circuit of FIG. 5A.

With reference to FIG. 5, there will be described a specific relation between the configuration of the heating block 251 and the control signals. FIG. 5A illustrates a configuration example of the heating block, and FIG. 5B illustrates the relation between the usage count of resistance (heating circuits) included in the heating block 251 and the amount of heat.

The heating block 251 as shown in FIG. 5A comprises the heating circuit where a plurality of series circuits (referred to as R-SW circuits) including resistance R and switch SW are connected in parallel with a power source (VSOURCE), and a decoding circuit (DECODE) 253 configured to control ON (close)/OFF (open) of the R-SW circuits upon receipt of the control signals from the heating control block 250. Assuming that the amounts of heat are equal when current passes through the individual resistance R, the amount of heat of the heating block is proportional to the number of the R-SW circuits where the current passes upon turned on, as shown in FIG. 5B, and thus the amount of heat can be controlled by controlling the number of the R-SW circuits. The heating control block 250 transmits to the heating block 251, the control signal HSIG corresponding to the number of the R-SW circuits to be turned on, on the basis of the previously obtained relation between the number of R-SW circuits and the amounts of heating. Upon receipt of the control signal from the heating control block 250, the decoding circuit 253 outputs the control signal HDEC being decoded, and controls the switch SW on and off.

In the example as shown in FIG. 5, the resistance R is labeled with one circuit symbol to represent each resistance. However, an actual circuit may comprise a plurality of resistances, connected in series or in parallel, in order to satisfy a predetermined resistance value or the maximum rated current. Similarly, the switch SW may comprises a plurality of switches connected in parallel, in order to satisfy the maximum rated current.

In FIG. 5, the variation of the resistance value controls the amount of heat. Alternatively, the amount of heat may be controlled according to control of a source voltage value, control of a current value, ON/OFF time control of resistance, or a count for driving an oscillator such as a ring oscillator.

Figure 6:
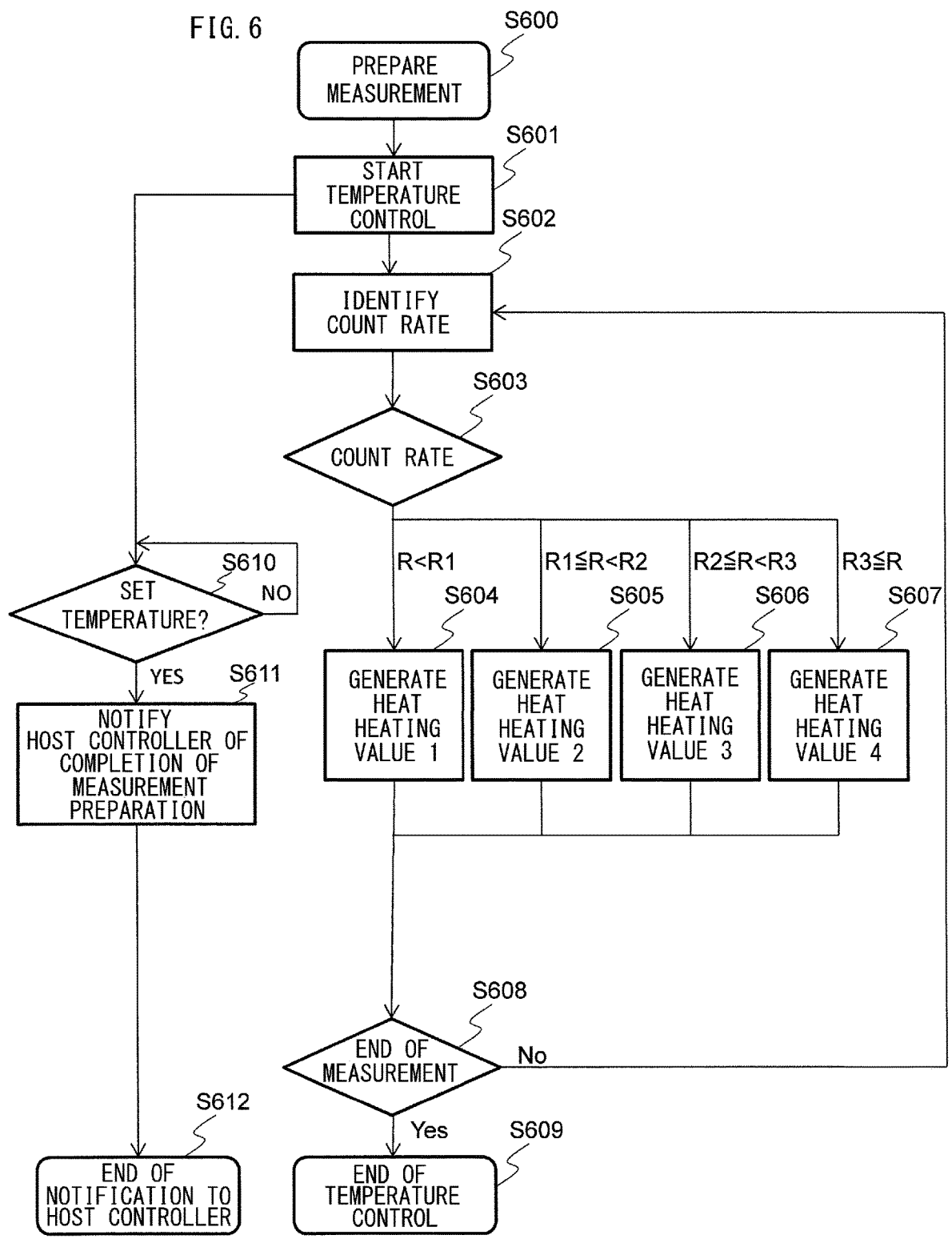
FIG. 6 is a flowchart showing the heat amount control relating to the first embodiment.

Next, with reference to the flowchart as shown in FIG. 6, the heat amount control according to the heating control block 250 will be described. Firstly, in order to start measurement by the X-ray CT apparatus, the heating control block 250 is notified of a measurement setup from the host controller, for example, from a controller of the X-ray CT apparatus (S600). Then, temperature control can be started immediately after the measurement (S601).

In the temperature control, in response to the count rate, the heat amount control operation (S602 to S608) and the temperature monitoring operation (S610 to S612) are performed in parallel. In the heat amount control operation, for example, the count rate is identified on an imaging view basis (S602), and the amount of heat is determined in response to this count rate R thus identified (S603). In the illustrated example, the control is performed in a manner that divides R into four stages in ascending order, and allocates the amounts of heat different from one another to the stages, respectively (S604 to S607). It is to be noted that the number of the stages for controlling the amount of heat is not necessarily four, and it may be increased or decreased as needed. The amount of heat in response to the count rate is determined by the count rate and the amount of heat (additional power consumption Padd) as shown in FIG. 2. For example, it is preferable to create a table where the relation between the count rate and the amount of heat is obtained in advance, as to each of the heating blocks 251A to 251F as shown in FIG. 4.

FIG. 7 shows an example of the tables providing the relation between the count rate and the amount of heat with respect to each heating block. In the example as shown in FIG. 7, the tables are created to show the relation between each output (COUT) from the counter 274 and the amount of heat. This is because, in general, in the counter with the lower threshold VTH, the higher is the count rate, and as the threshold VTH becomes higher, the count rate is lowered accordingly. FIG. 7A shows a table providing the amounts of heat of the heating blocks 251-A to 251-D, placed in proximity to the circuit components (CSA, HPF, CMP, and CNT) in the top line of FIG. 4. FIG. 7B shows a table providing the amount of heat of the heating blocks 251-E and 251-F placed in proximity to the circuit components (CMP, CNT) 273-2 and 274-2 placed in the second line and following lines, this table does not include the circuit components 271 and 272 that are commonly used in each line of the heating blocks.

Power consumption at each photon count rate is calculated according to circuit simulation or other similar methods, and further calculation is performed to obtain the amounts of heat in heating elements necessary for the constant control of the amount of heat, whereby the tables above can be created. By way of example, assume that a magnitude relation is found in the thresholds VTH1, VTH2 . . . for the peak value determination as shown in FIG. 4, such as VTH1≤VTH2≤ . . . . In order to acquire the activated state of the circuit blocks (CSA and HPF) most properly, before a current pulse enters the voltage comparators (CMP), it is necessary to calculate the photon count rate by using the count value COUT1 that is obtained by counting the pulse at the lowest threshold. In addition, in order to acquire the activated state of the circuit blocks (CMP, CNT) in the first line, it is necessary to use the photon count rate that is calculated by using the count value COUT1 in a similar manner. Therefore, the amounts of heat of the heating blocks 251-A to 251-D are determined on the basis of the photon count rate calculated from the count value COUT1.

Next, in order to acquire the activated state of the circuit blocks (CMP 273, CNT 274) in the second line, it is necessary to use the photon count rate calculated by using the count value COUT2. Therefore, the amounts of heat of the heating blocks 251E and 251F are determined on the basis of the photon count rate calculated from the count value COUT2. Similarly in the subsequent process, the correspondence table is created as required, in response to the number of combinations of the voltage comparators 273 and the counter 274, thereby allowing simple calculation of a necessary amount of heat from the photon count rate. When there is strong linearity among the correspondence tables being provided and interpolation such as constant multiplication is applicable, creation of some of the correspondence tables may be skipped as required. In manufacturing LSI, variations are likely to occur. Therefore, those tables can be used after correction of data on the basis of actual measurement, and this may achieve more accurate heat amount control.

With the use of such tables as described above, the heating control block 250 obtains the amount of heat P necessary for each heating block, using as inputs, the photon count rate R being the count values COUT1, COUT2 . . . and delivers the control signal HSIG to each heating block, in association with P.

After implementing the heat amount control according to the count rate (S603 to S607), it is checked whether or not there is notification of measurement end from the host controller (S608), and if the measurement has not been completed yet, the count rate is identified again (S602). On the other hand, when the notification of measurement end is confirmed, the temperature control is completed (S609). There will now be described the temperature monitoring operation that is performed in parallel with the operation as described above. The chip 23 (LSI) as a target for temperature management has relatively low thermal capacity, and thus it is likely to reach a predetermined temperature at steady state in seconds. This time length until reaching the temperature at steady state is shorter than the time required for rotational acceleration of the scanner in the CT apparatus, for instance. Therefore, the LSI where the chip 23 is formed becomes the state where the temperature is already managed before starting the actual measurement. Furthermore, after starting the temperature control (S601), it is confirmed using a means such as a temperature sensor or a timer, whether the temperature has reached the predetermined temperature at steady state (whether the time for reaching the temperature at steady state has elapsed) (S610), and the host controller is notified of the completion of measurement preparation (S611 to S612). Accordingly, erroneous operations such as starting the measurement before reaching the temperature at steady state can be avoided, achieving safe control.

There has been described the case where the heat amount control is performed with identifying the count rate on an imaging view basis. The interval for identifying the count rate, that is, the interval for controlling the additional amount of heat may be shorter than the time constant of temperature change in a system for managing the temperature. For detectors placed in a region where variation in the photon count rate is small, the interval for controlling the amount of heat may be extended as appropriate. In addition, the interval for controlling the amount of heat may vary depending on the positions of the module 20 or the detectors in the X-ray detector 2. For example, the interval for controlling the amount of heat may be extended as appropriate for the detector elements that are placed in a region other than the central part of the X-ray detector 2, where variation in the photon count rate is small.

As described above, according to the present embodiment, the heating block (heating element) is arranged for each of the circuit components constituting the counting block 231 of the chip 23, and each heating block is controlled, on the basis of the count rate being the output of the counting block, and the previously obtained relational tables between the count rate and the amount of heat for every heating block, thereby allowing the temperature of the counting block 231 to be kept nearly constant, irrespective of the variation in the count rate, and preventing change of the count rate performance caused by the temperature change in the circuit components.

According to the present embodiment, feedback control of the amount of heat is performed at intervals shorter than the time constant at which the temperature changes in the system for managing the temperature, and therefore it is possible to reduce the amount of temperature change in the system for managing the temperature. Furthermore, according to the present embodiment, the period for performing the temperature control, that is, the period of redundant heating, is limited during the measurement, and this may produce an effect that power consumption of the overall counting block (LSI) including the heating blocks is reduced.

Furthermore, the present embodiment (the example as shown in FIG. 4) provides a configuration that the amount of heat is controlled pixel by pixel, that is, on a counting block PB basis, so as to maintain the constant temperature in the circuit operation. Therefore, even under the operating condition where the photon count rate varies drastically between adjacent pixels, the operating temperature of the circuit is kept constant, producing an effect that a stable image can be acquired.

As described above, in the present embodiment, heating blocks functioning as the heat amount compensator are placed for the respective circuit components of the counting block. The present embodiment is not limited to the example as shown in the figures, and it may be variously modified. For example, in FIG. 4, the heating blocks are provided respectively for the circuit blocks (CSA, HPF, CMP, CNT), but the heating block may be unnecessary for the circuit block with low temperature sensitivity. Alternatively, a plurality of heating blocks may be collected as one heating block, to the extent that this may not interfere with the purpose for maintaining the operating temperature to be constant in the circuit block.

In FIG. 4, the photon counting result COUT is used as the information for the heat amount control block to determine the amount of heat, but information other than the photon counting result COUT can be used. For example, the amount of heat may be determined on the basis of the temperature information acquired from a thermometer implemented within the counting block 231 (LSI) or in proximity to the LSI, or on the basis of the current information acquired from an ammeter implemented within the LSI or in a power circuit for the LSI.

Next, there will be described a modified example of the first embodiment of the X-ray CT apparatus provided with the heating blocks, similar to the first embodiment, but the position of the heating blocks are different therefrom.

Modification of the First Embodiment

In the first embodiment, the heating block is provided in proximity to each of the circuit blocks constituting the counting block. In the present modified example, the heating blocks are placed between the counting blocks adjacent to each other. There will now be described the present modified example, focusing on the points different from the first embodiment. In the present modified example, an example where the present invention is applied to the X-ray detector of the X-ray CT apparatus will be described, similar to the first embodiment, and some figures used for describing the first embodiment may also be referred to as required.

Figure 8:
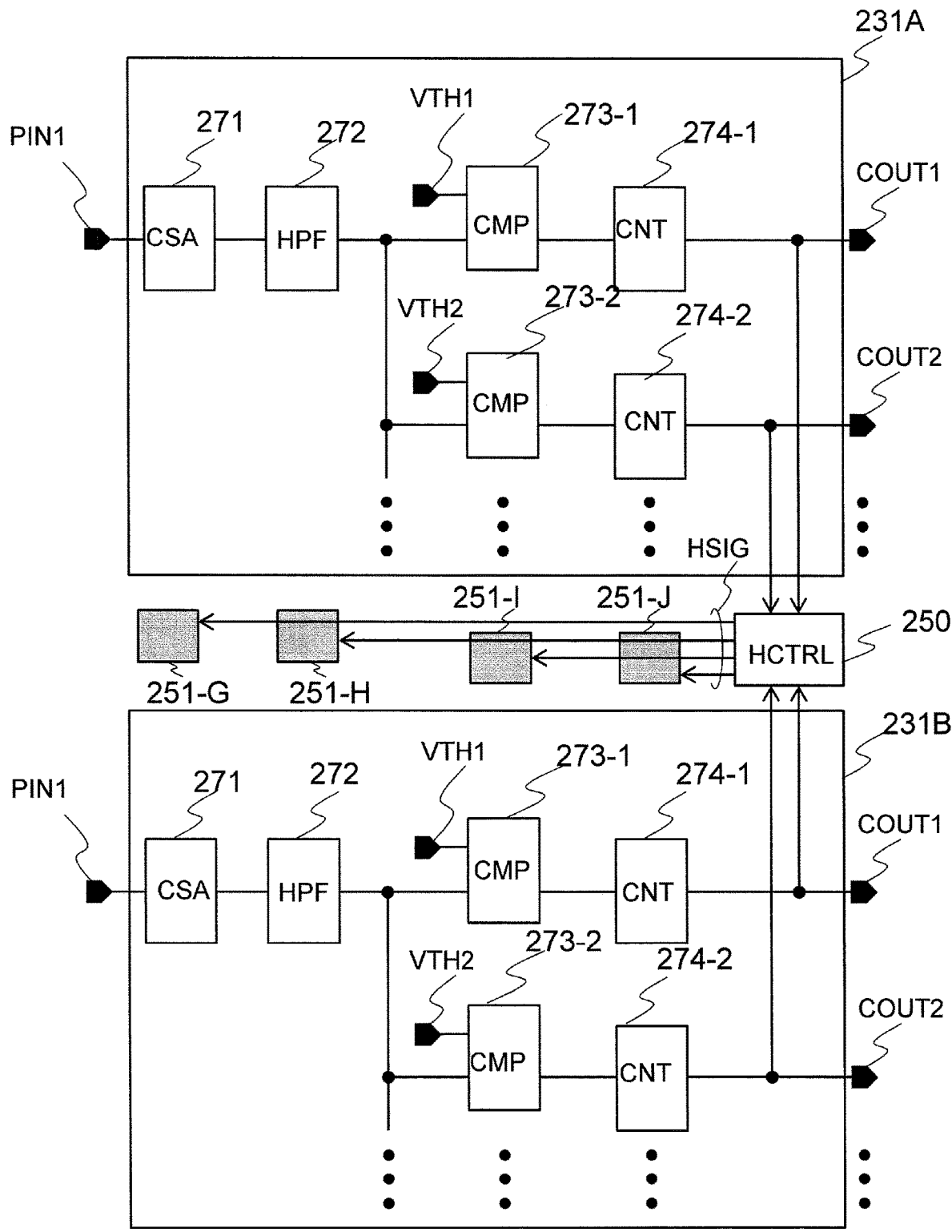
FIG. 8 is a block diagram showing a configuration of the counting circuits relating to a modified example of the first embodiment.

FIG. 8 illustrates the chip 23 of the present modified example. Hereinafter, in FIG. 8, elements with the same functions as FIG. 4 are labeled with the same reference numerals, and they will not be described redundantly. Two counting blocks 231A and 231B shown in FIG. 8 indicate two adjacent counting blocks, out of the multiple counting blocks 231 included in the chip (LSI) 23 as shown in FIG. 3B.

As illustrated, each of the counting blocks 231A and 231B has the same configuration as a conventional counting block, configuring a counting circuit having inputs from the input PIN1, different values of the threshold VTH1, VTH2 . . . and outputs of the number of photons COUT1, COUT2 . . . . This counting circuit is provided with a charge amplifier (CSA) and a high-pass filter (HPF) commonly used at every X-ray energy level, and comparators (CMP) and counters (CNT) respectively associated with the X-ray energy levels.

There are provided between those two counting blocks 231A and 231B, the heating blocks 251G to 251J, functioning as the heat amount compensator 25, and the heating control blocks 250 for controlling these heating blocks. The internal structure of each heating block 251 is the same as the heating block 251 of the first embodiment, and it may have the circuit configuration as shown in FIG. 5A.

In such a configuration as described above, the heating control block 250 is notified of the count value COUT from each photon counting block 231, and on the basis of thus notified count values, amounts of heat in the heating block charge amplifier 271 and in the high-pass filter 272 are determined. These amounts of heat are determined according to a means such as simulation so that the temperature in the circuit blocks (CSA, HPF, CMP, CNT) becomes constant, considering temperature gradient of the heating blocks 251 and the circuit blocks (CSA, HPF, CMP, CNT) within the two counting blocks 231A and 231B, with respect to the count rate. Also in the present modified example, a table indicating the relation between the photon count rate and the amount of heat may be created in advance as to each of the heating blocks, as shown in FIG. 7.

Procedures of the heat amount control of the present modified example are the same as the first embodiment. As shown in FIG. 6, the control is performed at predetermined intervals, from the start to the end of the measurement, so that the temperature in the chip 23 is kept nearly constant, irrespective of the variation in the count rate. As described in the first embodiment, the additional heat amount control may be performed in a measurement view basis, or at intervals shorter than the time constant of the temperature change in the system for managing temperature. In addition, the interval of the heat amount control may be extended as appropriate for a detector placed in a region where the variation in the photon count rate is small.

According to the present modified example, in addition to the effects of the first embodiment, the heating control block and the heating blocks are shared by the multiple counting blocks, thereby providing an advantage in that the area of layout can be reduced.

The example shown in FIG. 8 illustrates that two photon counting blocks 231A and 231B share one heat amount compensator 25 comprising the heating control block 250 and a plurality of heating blocks 251. The ratio for the sharing (the ratio of the number of the heat amount compensators to the number of the photon counting blocks) may be changed as appropriate, such as sharing I heat amount compensators with respect to J photon counting blocks 231 (I<J). Furthermore, in the present modified example, the heat amount compensator (the heating control block 250 and the heating blocks 251) is arranged between the photon counting blocks, but it may be placed in any space within the photon counting block, or any space in the LSI where the counting blocks are formed.

Second Embodiment

In the first embodiment and its modified example, the heating circuit generating heat from itself is added to the counting block, functioning as the heat amount compensator. The present embodiment features that a pseudo pulse is generated in association with the count rate, and the activity state of the circuit components constituting the counting block is controlled to be the same between the time of low count rate and the time of high count rate.

There will now be described the present embodiment, taking the radiation detector of the X-ray CT apparatus as an example, similar to the first embodiment. Also in the present embodiment some figures used for describing the first embodiment may be referred to as required.

Figure 9:
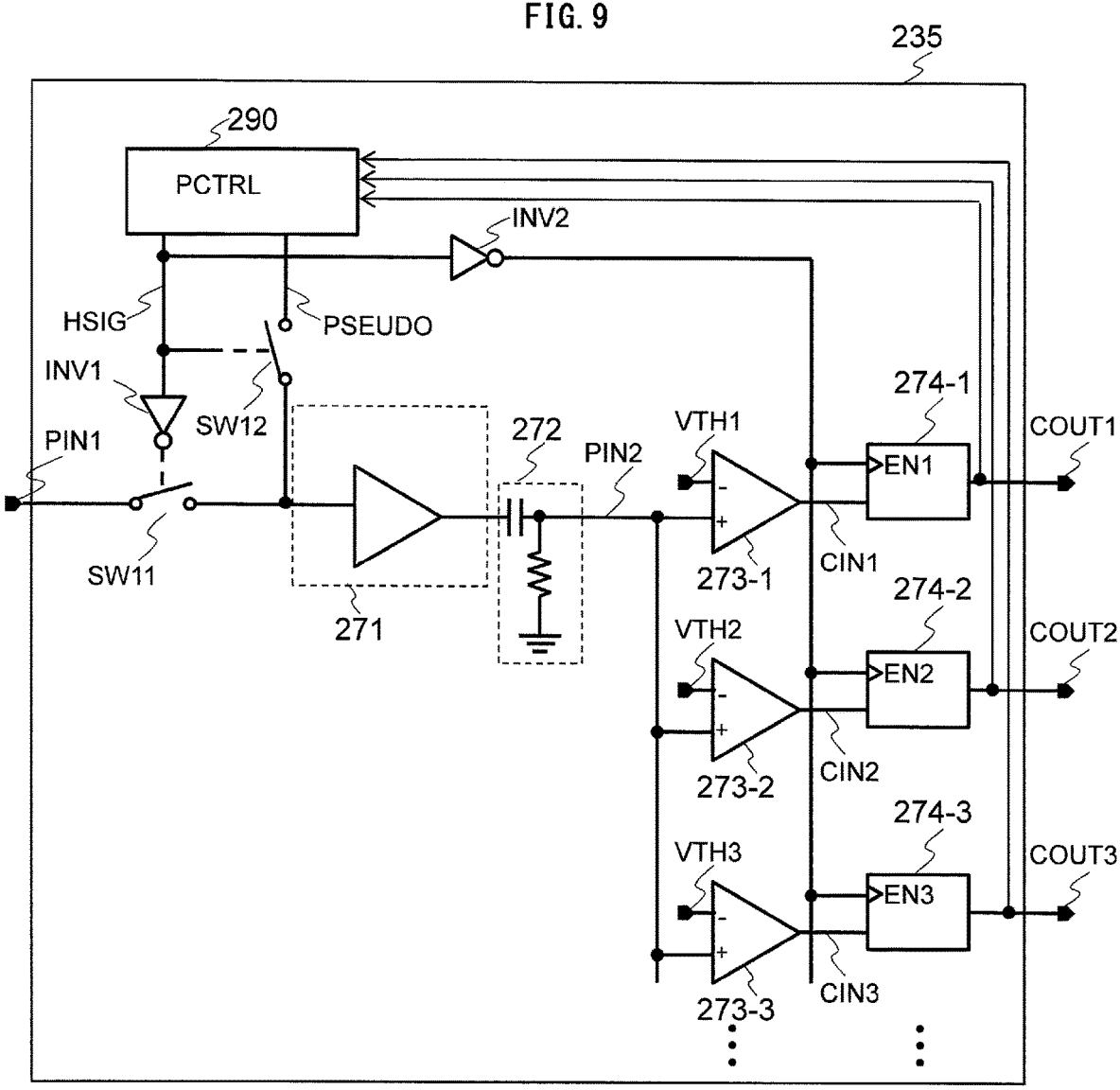
FIG. 9 is a block diagram showing a configuration of the counting circuit according to a second embodiment.

FIG. 9 shows an example of the counting block 235 in the X-ray detector 2 according to the present embodiment. This counting block 235 represents one of the multiple counting blocks constituting the chip 23 as shown in FIG. 3B, and the other counting blocks have the same configuration. In FIG. 9, elements having the same function as the circuit elements in FIGS. 3 and 8, are shown as representative circuit elements implementing such functions, each indicated as a block surrounded by a rectangular form and labeled with the same reference symbol. Descriptions will be provided, focusing on different points, without describing redundantly as to each of the elements.

The counting block 235 is provided with the circuit components comprising the charge amplifier (CSA) 271, the high-pass filter (HPF) 272, a plurality of voltage comparators (CMP) 273 and a plurality of counters (CNT) 274, and further provided with a pseudo pulse generator 290, a switch SW11 inserted between the input PIN1 and the charge amplifier 271, and a switch SW12 inserted between the pseudo pulse generator 290 and the charge amplifier 271.

The pseudo pulse generator 290 outputs a control signal HSIG, along with outputting a pseudo pulse PSEUDO via a signal line to which the switch SW12 is connected. The control signal HSIG is connected to the switch SW12 and the inverters INV1 and INV2. An output of the inverter INV1 is connected to the switch SW11. An output of the inverter INV2 is connected to the input terminals EN1, EN2, and EN3 controlling activation and stop of each counter. The outputs COUT1, COUT2 . . . from the respective counters are fed back to the pseudo pulse generator 290.

Next, the operation of the photon counting block 235 will be described. There are two operation modes in the photon counting block 235. One is a normal pulse measurement mode, and the other is a pseudo pulse generation mode that is activated when current inputs from the current input pin PIN1 are sparse. The count rate COUT inputted into the pseudo pulse generator 290 from each counter enables the mode switching. The pseudo pulse generator 290 sets the control signal HSIG to high level (H), thereby turning the SW12 ON (connected) and turning the SW11 OFF (unconnected), and the mode is switched to the pseudo pulse generation mode.

First, with reference to FIG. 10, the operation of the normal pulse measurement mode will be described. During the period of the normal pulse measurement, the control signal HSIG from the pseudo pulse generator 290 becomes L (low level), and the pseudo pulse PSEUDO is not generated. The counter control signals EN1, EN2, EN3 . . . inputted into the counters via the inverter INV2 become H (High level), and the counters are in the activated state. When current inputs from the current input pin PIN1 are generated at the time points T0, T2, and T4, the waveforms after passing through the high-pass filter (HPF) are shaped as indicated by PIN2 in FIG. 10, and the counter inputs CIN1, CIN2, and CIN3 are toggled at the time points T1, T3, and T5, in comparison with the threshold voltage VTH1, VTH2, VTH3 . . . . Strictly speaking, the time point when the counter input CIN is toggled is slightly delayed from the time point when PIN2 traverses each threshold voltage VTH, but these time points are treated as the same time in FIG. 10.

Figure 10:
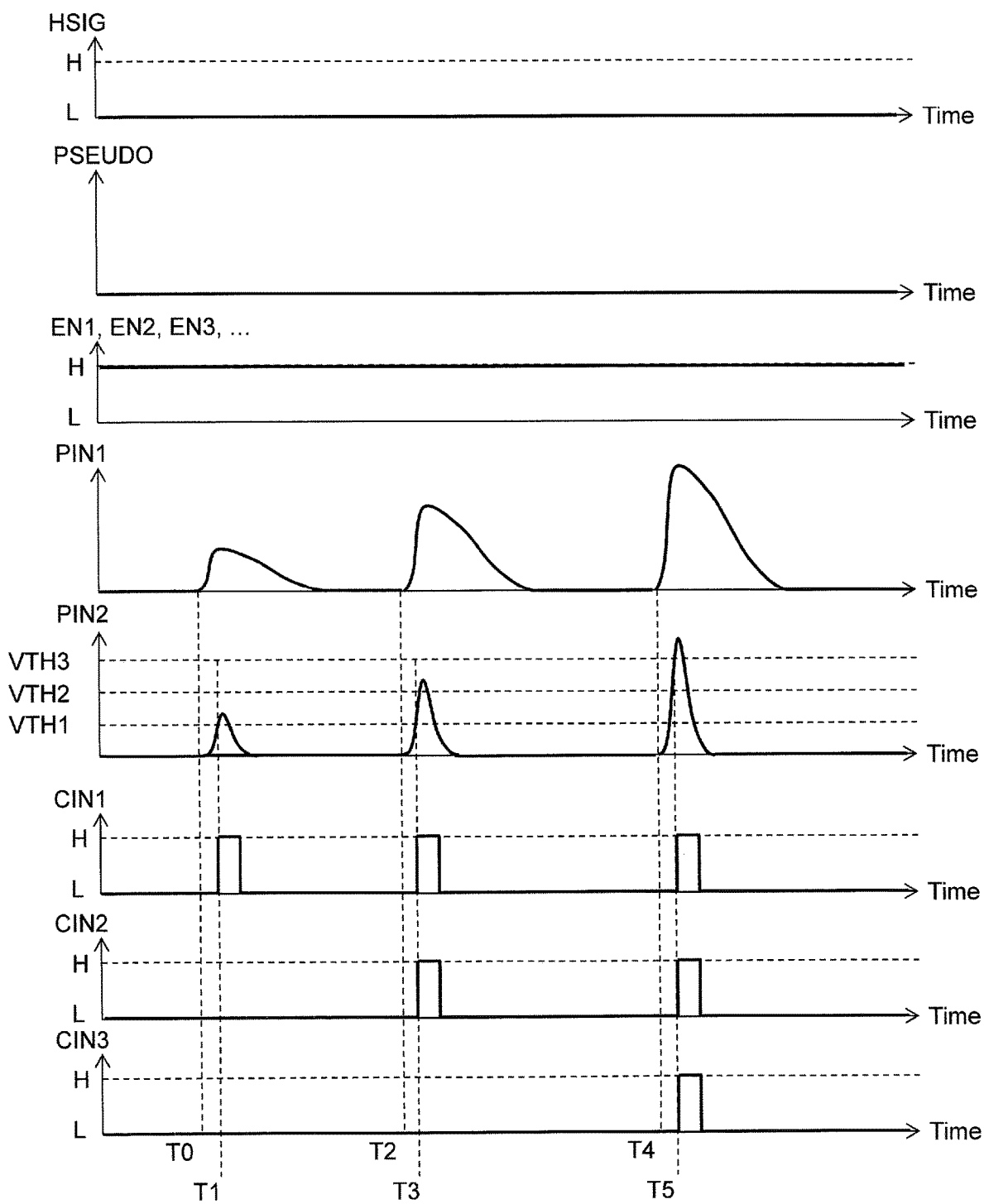
FIG. 10 shows operation waveform examples of the counting circuit according to the second embodiment.

In the pulse measurement method (referred to as pulse measurement method 1) as shown in FIG. 10, it is necessary to subtract the counter value COUT2 from the counter value COUT1, in order to obtain the number of pulses having a peak value that provides the threshold voltage equal to or higher than VTH1 and lower than VTH2. This is because, when a pulse with the peak value equal to or higher than VTH2 enters, not only the counter 274-2 but also the counter 274-1 is incremented. On the other hand, in a different pulse measurement method (referred to as pulse measurement method 2), the configuration of the voltage comparators and the counters is modified to achieve a circuit configuration where only the input CIN having the highest threshold voltage with respect to a certain peak value is selectively driven. In this case, for example, only CIN2 is toggled at the time point of T3, and only CIN3 is toggled at the time point of T5.

Figure 11:
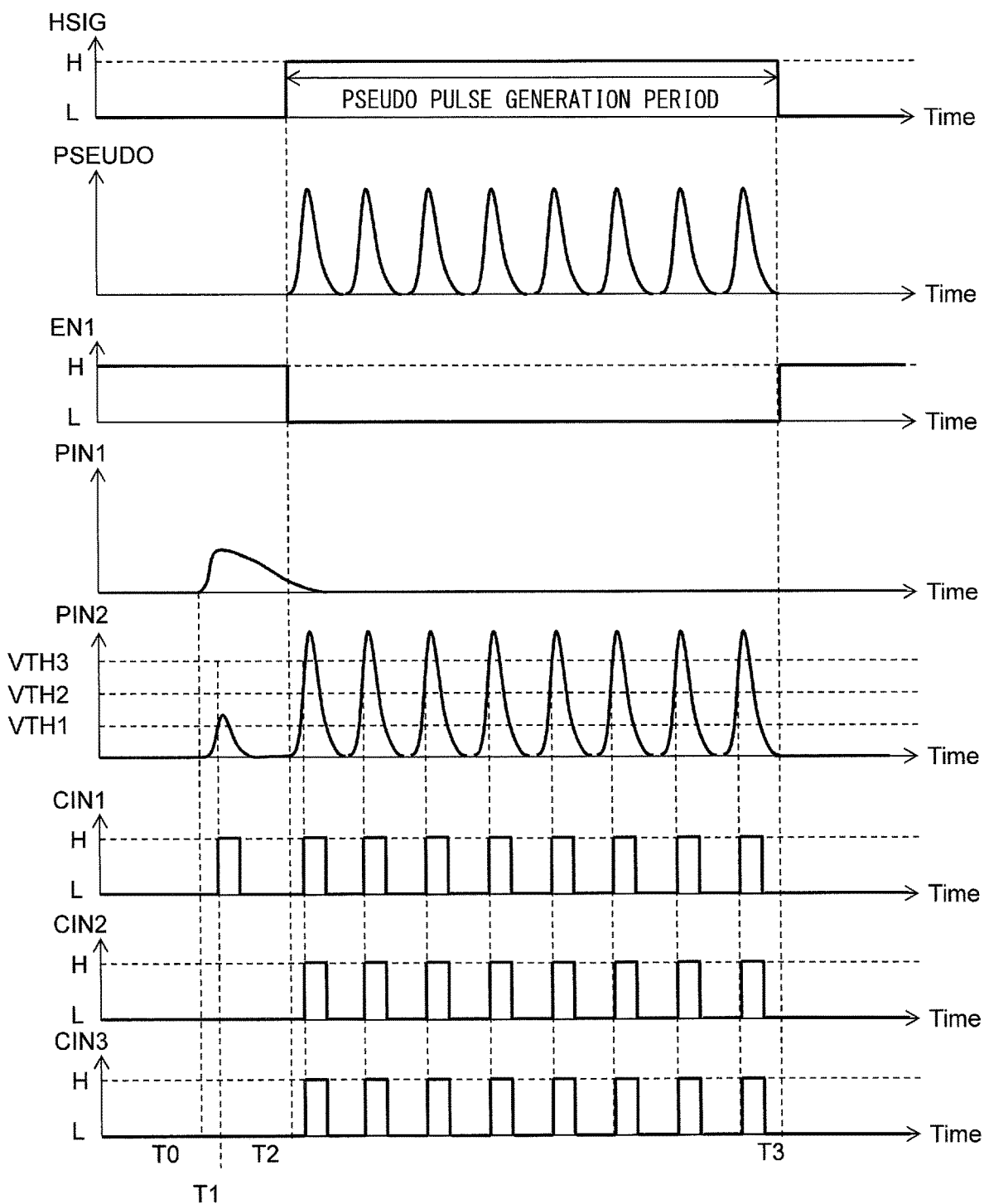
FIG. 11 shows operation waveform examples of the counting circuit according to the second embodiment.

Next, with reference to FIG. 11, there will be described an operation in the pseudo pulse generation mode. In the pseudo pulse generation mode, the current inputs from the current input pin PIN1 are extremely sparse, and therefore, pseudo pulses are generated during a period when there is no current input. For example, as shown in FIG. 11, immediately after a pulse generated in the semiconductor layer is inputted from the current input pin PIN1, the pseudo pulse generator 290 sets the control signal HSIG to H (high level), turning SW12 ON, thereby generating the pseudo pulse PSEUDO.

While those pseudo pulses are being generated, the counter control signals EN1, EN2, EN3 . . . inputted into the counter 274-1 . . . via the inverter 2 become L (low level), placing the counter in the suspended state. This may prevent increase of the counter value due to generation of the pseudo pulses. In the example as shown in FIG. 11, the pulse generated in the semiconductor layer at the time point T1 is inputted into the current input pin PIN1, and the counter input CIN1 is toggled at the time point T1. Thereafter, the period from the time points T2 to T3 corresponds to the period when pseudo pulses are generated, and for example, eight pseudo pulses PSEUDO are issued during this period. Then, the counter inputs CIN1, CIN2, CIN3 . . . are toggled. This toggling is masked since EN1, EN2, EN3 . . . are L (low level), and the counter value is not increased. FIG. 11 shows an example of control where pseudo pulses are generated with peak values allowing all the counters to be driven to increase additional power consumption. By controlling the peak value and the number of issued pseudo pulses, the amount of heat can be controlled as appropriate.

For this control, a correspondence table of the photon incidence rate, the peak value, and the number of issued pulses may be created, similar to the table as shown in FIG. 7, thereby enabling simple control. The pseudo pulse generation period may be configured as appropriate according to the photon incidence rate, so as not to interfere with counting of the photon incidence. For example, when the photon incidence rate is low, the pseudo pulse generation period is set to be long. On the other hand, when the photon incidence rate is high, the period is set to be short. The photon incidence rate that determines the pseudo pulse generation period may be obtained in advance, by preliminary measurement or other similar means.

In the example as shown in FIG. 9, outputs from the counters are fed back to the pseudo pulse generator 290, thereby switching between the two operation modes. However, a result obtained by the preliminary measurement may also be used for the switching of the operation modes, and when a predicted value of the incidence rate is low, the mode is switched to the pseudo pulse generation mode, whereas the mode is switched to normal, when a predicted value of the incidence rate is high. A threshold of the incidence rate for the mode switching may be preset. In addition, a method of forward control may be employed instead of the feedback control.

According to the present embodiment, generation of the pseudo pulses allows the control of the amount of heat of the chip 23, without affecting the counting result of the counter. In addition, according to the present embodiment, a specified circuit using a pulse input that is close to an actual pulse input is activated and power is consumed. Therefore, there is an advantage that the heating state of the circuit can be simulated with high fidelity. Also in the present embodiment, the additional heat amount control may be performed in a measurement-view basis, or at intervals shorter than the time constant of the temperature change in the system for managing temperature, as shown in FIG. 6. Alternatively, the interval for the heat amount control may be extended as appropriate for the detector placed in a region where the variation in the photon count rate is small.

Modification of the Second Embodiment

Figure 12:
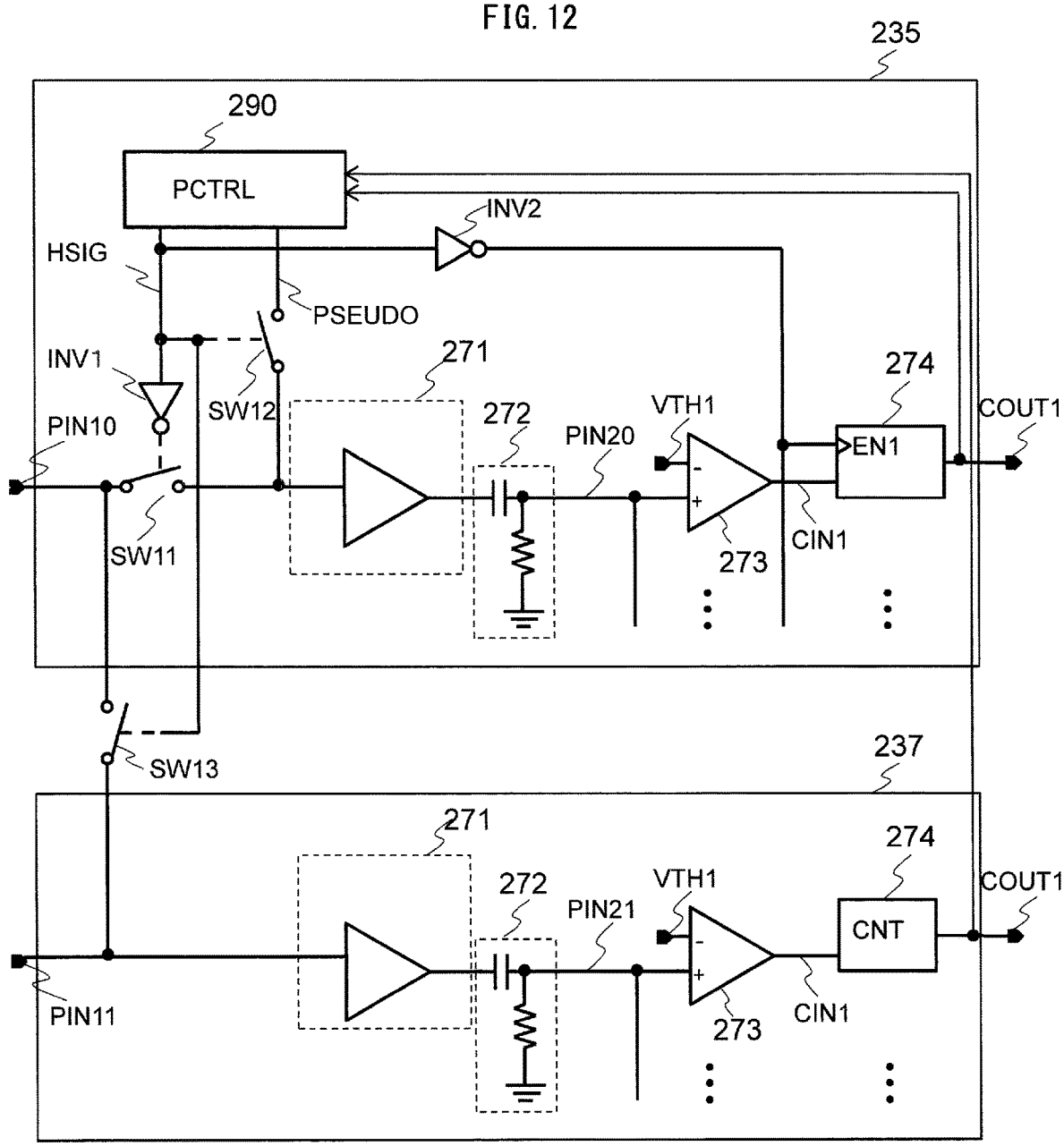
FIG. 12 is a block diagram showing a configuration of the photon-counting circuit relating to a modified example of the second embodiment.

In the second embodiment, there has been described that one pseudo pulse generator is provided for one counting block. In the present modified example, two or more counting blocks share one pseudo pulse generator. In other words, the ratio between the number of counting blocks and the number of the pseudo pulse generators are other than one-to-one. With reference to FIG. 12, there will be described the present modified example, focusing on the points different from the second embodiment. Hereinafter, in FIG. 12, elements with the same functions as FIG. 9 are labeled with the same reference numerals, and they will not be described redundantly.

Two counting blocks 235 and 237 as shown in FIG. 12 represent two of the multiple counting blocks constituting the chip 23 as shown in FIG. 3B, and the other counting blocks have the same configuration.

Similar to the counting block 235 of the second embodiment as shown in FIG. 9, the counting block 235 is provided with the pseudo pulse generator 290, the switch SW11 inserted between the input PIN10 and the charge amplifier 271, and the switch SW12 inserted between the pseudo pulse generator 290 and the charge amplifier 271, in addition to the circuit components (CSA, HPF, and a plurality of CMPs and CNTs) constituting the counting circuit. Though not illustrated in FIG. 12, this counting block 235 is also provided with a plurality of pairs of the voltage comparators 273 and the counter 274, in association with a plurality of energy levels. Similar to the second embodiment, when the control signal HSIG of the pseudo pulse generator 290 is high level (H), the switch SW12 is turned ON (connected state), and pseudo pulses are generated along with setting the inputs EN1, EN2 . . . of the counters to be low level.

On the other hand, the counting block 237 is not provided with an additional circuit component, such as the pseudo pulse generator 290. It is to be noted that a switch SW13 is connected between the input pin PIN11 of the counting block 237 and the input pin PIN10 of the counting block 235. The switch SW13 is turned ON and OFF by the control signal HSIG from the pseudo pulse generator 290, similar to the switch SW12. When the signal HSIG is high level (during the pseudo pulse generation mode), the switch is turned ON, allowing both an input from the input PIN10 of the counting block 235 and an input from the input PIN11 of the counting block 237 to enter the counting block 237.

Next, the operation of the photon counting blocks 235 and 237 of the present modified example will be described. Also in the present modified example, there are two operation modes, the normal operation mode and the pseudo pulse generation mode. In the normal operation mode where the photon incidence rate is high, the switch SW11 is closed and the switches SW12 and SW13 are open according to the control by the pseudo pulse generator 290, and thus no pseudo pulse PSEUDO is generated. In other words, the photon counting blocks 235 and 237 count the current pulses respectively from the current input pins PIN10 and PIN11.

On the other hand, in the pseudo pulse generation mode where the photon incidence rate is low, according to the control by the pseudo pulse generator 290, the switch SW11 is open, and the switches SW12 and SW13 are closed, and then pseudo pulses are generated. At this time, the current pulses from the current input pins PIN10 and PIN11 are counted collectively in the photon counting block 237. In this situation, the photon counting block 235 operates constantly in the pseudo pulse mode, and generates additional power consumption. Switching the modes, and controlling the period for issuing the pseudo pulses and the number thereof are the same as the second embodiment. This control is performed according to the feedback control using outputs from the counters, or using the tables provided in advance (corresponding tables like the tables as shown in FIG. 7) or the count rate of preliminary counting.

Since the switch SW11 is open during the pseudo pulse generation period, counting in the counting block 235 is not performed. However, a result of counting in the photon counting block 235 is generated and complemented as appropriate by using the counting result in the photon counting block 237. There is considered as a method for the complement, for example, a half of the counting result in the photon counting block 237 may be used as an estimate value of the counting result in each of the two photon counting blocks 235 and 237. It is further possible to estimate each counting block, from the counting results in the surrounding counting blocks (pixels). In this case, for example, when failing to count in a certain counting block, a gradient of the number of incident photons is obtained from counting results of the front and back or the left and right of the counting block, and the counting result is divided proportionally according to the gradient, so as to be used as the counting estimate values in the photon counting blocks 235 and 237.

Also in this modified example, the operation period and the number of generated pseudo pulses in the pseudo pulse mode may be changed appropriately according to the photon incidence rate. Similar to the aforementioned embodiments, the control of the additional amount of heat may be performed in a measurement-view basis, or at intervals shorter than the time constant of the temperature change in the system for managing the temperature. For detectors placed in a region where the variation in the photon count rate is small, the interval for controlling the amount of heat may be extended as required.

According to the modified example, in addition to the effect similar to the second embodiment, the photon counting block for measuring current pulses is separated from the photon counting block that is operated in the pseudo pulse mode, and thereby producing an advantage that a circuit area can be used effectively. In this modified example, the ratio between the photon counting block for performing photon counting and the photon counting block operating in the pseudo pulse mode is one-to-one, but this ratio may be changed as appropriate.

Third Embodiment

The present embodiment features that the counting circuit is provided with a circuit enabling the counter to perform redundant operation (counter redundant-operation circuit), functioning as the heat amount compensator, and this redundant operation of the counter allows generation and control of additional power consumption. As the counter redundant-operation circuit, a publicly known up-down counter may be employed, which repeats signal increment and decrement, for instance.

Figure 13:
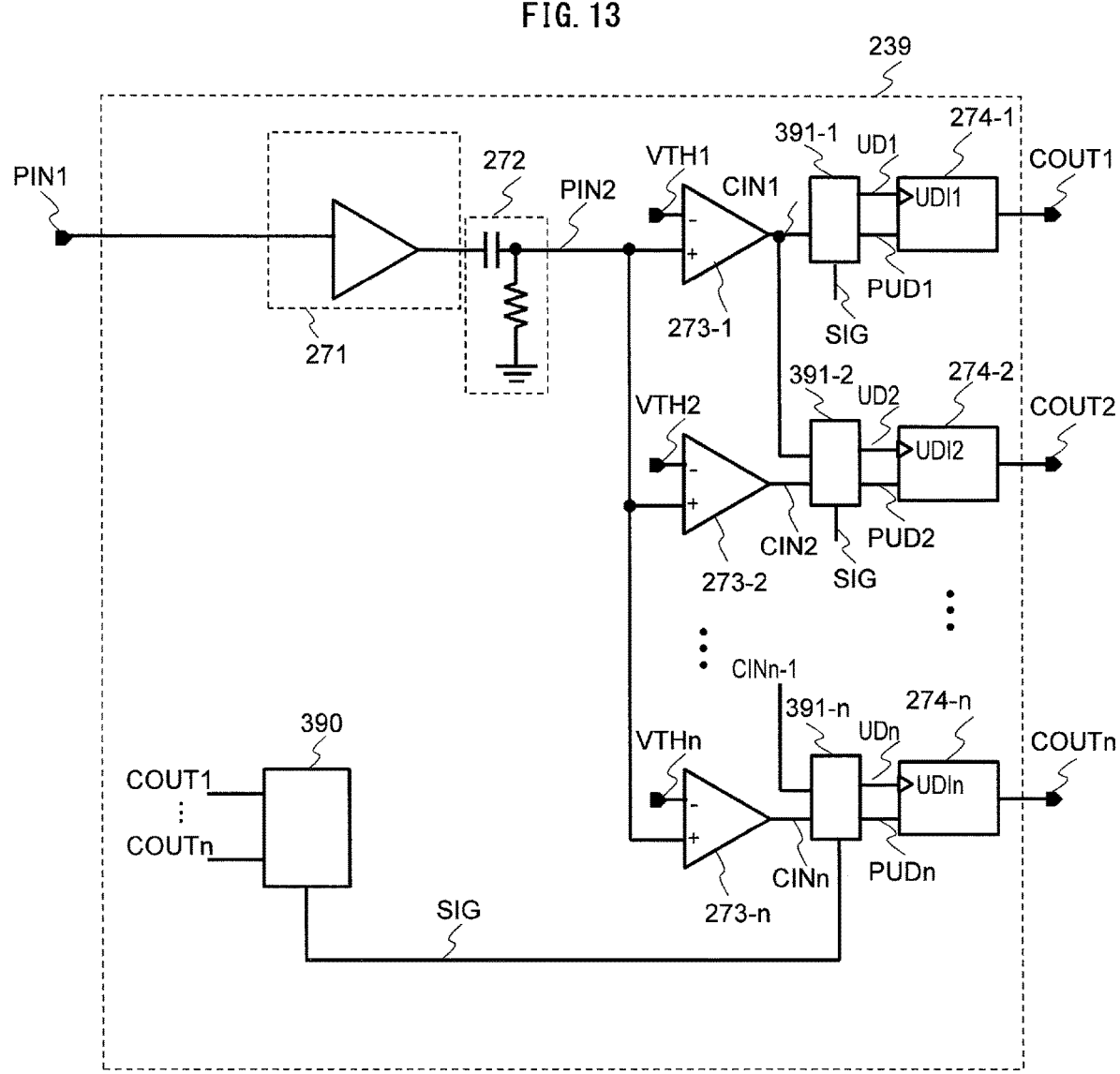
FIG. 13 is a block diagram showing a configuration of the photon-counting circuit according to a third embodiment.

With reference to FIG. 13, there will be described the counting circuit of the third embodiment. Here, an example will be described where the present invention is applied to the radiation detector of the X-ray CT apparatus. In FIG. 13, elements with the same functions as FIGS. 9 and 12 are labeled with the same reference numerals, and they will not be redundantly described.

The counting block 239 of the present embodiment as shown in FIG. 13 indicates one specific counting block, out of the multiple counting blocks constituting the chip 23 as shown in FIG. 3B. As illustrated, the counter redundant-operation circuits 391-1, 391-2 . . . 391-$n$ are inserted in series between the voltage comparators 273 and the counters 274 in respective lines, and there is also added a photon incidence rate decision circuit 390 for controlling the counter redundant-operation circuits. The photon incidence rate decision circuit 390 receives COUT1, COUT2 . . . . COUTn, which are outputted from the respective counters 274. The photon incidence rate decision circuit 390 sends control signals SIG respectively to the counter redundant-operation circuits 391-1, 391-2 . . . 391-$n$, on the basis of thus inputted values.

In the counting block 239, a flow of signals from the input PIN1 to each of the voltage comparators 273 is the same as the normal counting block. A notification of a comparison result CINm in the voltage comparator 273-$m$ using a specific threshold VTHm is provided not only to the counter redundant-operation circuit 391-$m$, but also to the counter redundant-operation circuit 391-$m$+1 to which the voltage comparators 273-$m$+1 is connected where one-level higher VTH(m+1) is inputted. By way of example, notification of the output CIN1 from the voltage comparator 273-1 is provided not only to the counter redundant-operation circuit 391-1, but also to the counter redundant-operation circuit 391-1. The counters (274-1 . . . 274-$n$) receive respectively from the counter redundant-operation circuits, signals (PUD) for selecting up or down the counter value, and pulse-like signals (UD).

Figure 14:
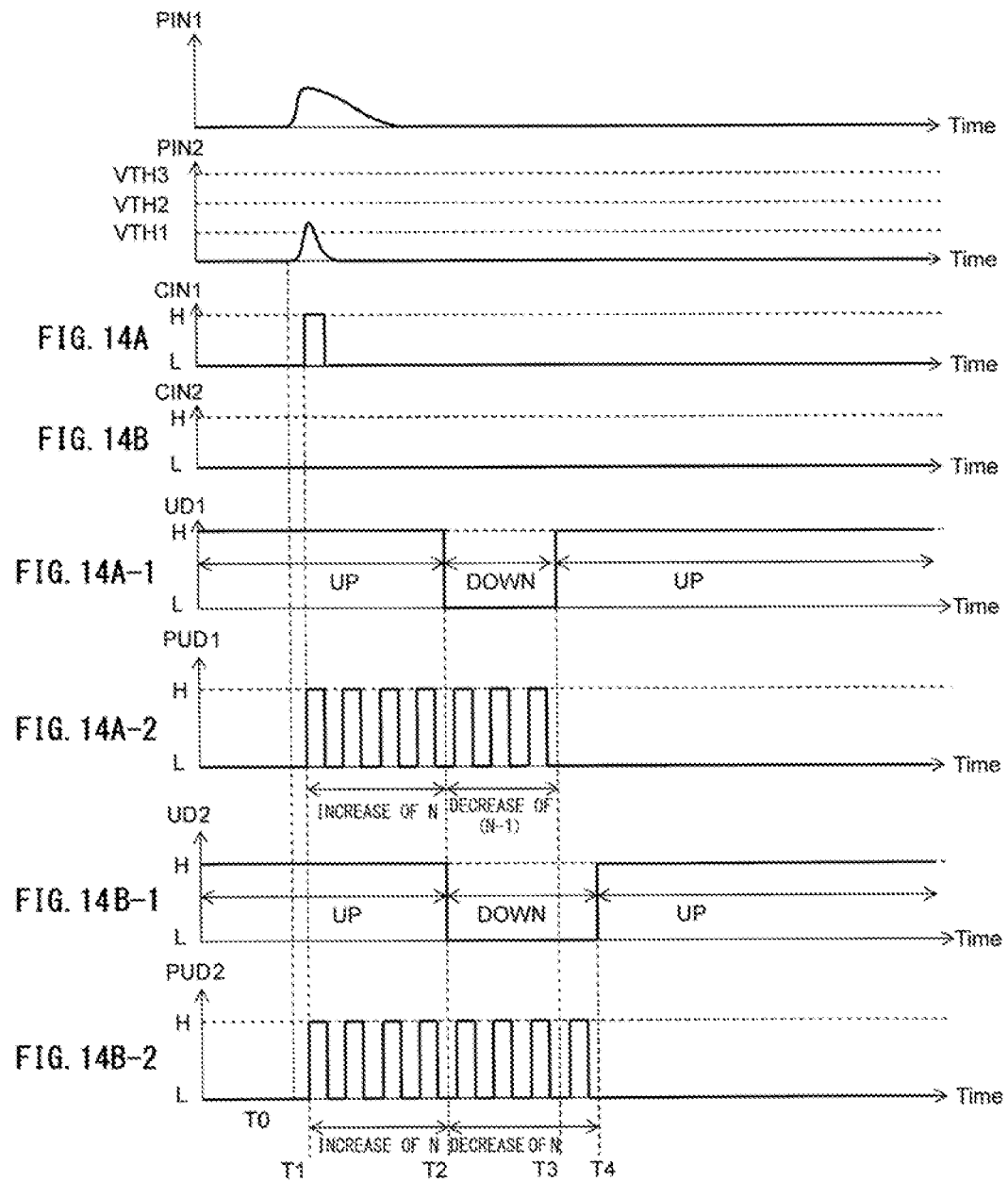
FIG. 14 shows operation waveform examples of the counting circuit according to the third embodiment.

With reference to FIG. 14, an operation of the counting block in the aforementioned configuration will be described. At the time point T0, a current pulse from the semiconductor layer is inputted via the current input pin PIN1. Then, the pulse passes through the charge amplifier 271 and is shaped by the high-pass filter 272 (PIN2). As a result of comparison with a predetermined voltage threshold VTH1 in the voltage comparator 273-1, the input CIN1 to the counter 274-1 is toggled at the time point T1 (FIG. 14A). The input CIN1 is inputted to each of the counter redundant-operation circuits 391-1 and 391-2. Since the current pulse is lower than the threshold VTH2 of the voltage comparator 273-2, the input CIN2 into the counter 274-2 is not toggled (FIG. 14B). Therefore, only CIN1 is inputted into the counter redundant-operation circuit 391-2.

As indicated by FIG. 14A-1, when the input CIN1 is received, the counter redundant-operation circuit 391-1 instructs to set the counter up-down control signal UD1 to H (high level), i.e., "increase of the counter value" continuously from the time point T1 to the time point T2, and then, to L (low level) i.e., "decrease of the counter value" from the time points T2 to T3. On the other hand, as shown in FIG. 14B-1, the counter redundant-operation circuit 391-2, instructs to set the counter up-down control signal UD2 to H (high level), i.e., "increase of the counter value" continuously from the time point T1 to the time point T2, and then, to L (low level) i.e., "decrease of the counter value" from the time points T2 to T4.

In parallel to this operation, the counter redundant-operation circuit 391-1 generates (2N-1) times toggles in total, combining with the toggling in sync with CIN1, in the counter input PUD1 (FIG. 14A-2). On the other hand, the counter redundant-operation circuit 391-2 generates 2N toggles in total in the counter input PUD2 (FIG. 14B-2). As a result, a transition of the counter values of the counters 274-1 and 274-2 takes place from the time points T1 to T4 indicates+1, ±0 with respect to the original value (M=1, in this example). In other words, the count value does not change from an intended count value. In addition, the redundant operation performed in this counting operation allows much more power consumption than the normal operation.

In this situation, the photon incidence rate decision circuit 390 that receives counter outputs COUT1 to COUTn, controls the intervals of the up-down signal UD and the number of PUD counts from the counter redundant-operation circuit, thereby controlling the count of redundant toggling operations and adjusting the additional power consumption.

In the descriptions above, the counter (the counter redundant-operation circuit) connected to the voltage comparator having a threshold one level higher than a certain threshold is subjected to the redundant operation. Simultaneously with this operation, another counter connected to the voltage comparator having rather higher threshold may also be subjected to the redundant operation, thereby allowing generation of much more additional power consumption. This provides the connection mode where a plurality of counter redundant-operation circuits 391-$m$ to 391-$m$+n is also notified of the comparison result CINm from the voltage comparator 273-$m$ with the threshold VTHm. The additional power consumption can be adjusted flexibly, by appropriately selecting the redundant operation volume of the counter and the number of counters where the redundant operation is performed. In this case, the number of counters where the redundant operation is performed may be fixed, or changed appropriately during the chip operation. In addition, the redundant toggling period may be set as appropriate according to the photon incidence rate, so that the period may not interfere with the photon incidence count. By way of example, when the photon incidence rate is low, long-time redundant toggling may be performed many times, whereas the period may be made short with reducing the number of the redundant toggling times, when the photon incidence rate is high.

According to the present embodiment, only addition of the simple logical circuit into the photon counting block enables the control of the amount of heat, providing an advantage that reduces overhead of the circuit area.

Modified Example of the Third Embodiment

Figure 15:
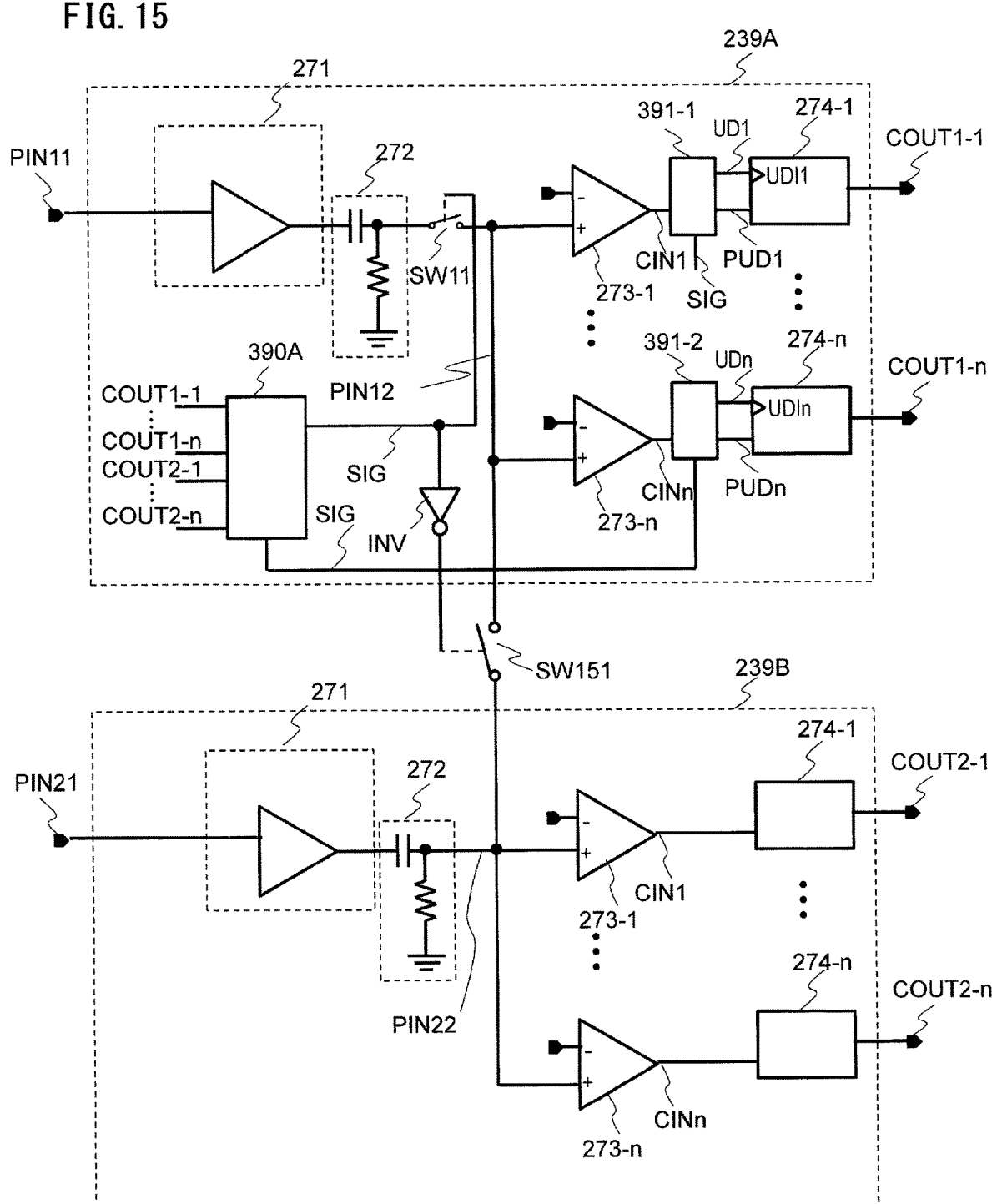
FIG. 15 is a block diagram showing the counting circuits relating to a modified example of the third embodiment.

In the third embodiment, the counter redundant operation is controlled in individual counting blocks. The present modified example features that a plurality of counting blocks is activated in one group, during the operation mode where the count rate is low. With reference to FIG. 15, as an example of the radiation detector of the present modification, the radiation detector used in the X-ray CT apparatus will be described. In FIG. 15, elements identical to those as shown in FIG. 13 are labeled with the same reference symbols, and they will not be described redundantly.

The photon counting blocks 239A and 239B as shown in FIG. 15 are adjacent to each other. Similar to the counting block 239 of FIG. 13, one of the counting blocks 239A is provided with the counter redundant-operation circuits 391 and the photon incidence rate decision circuit 390A. In the photon incidence rate decision circuit 390 of the third embodiment, only the count value of the counting block where this photon incidence rate decision circuit is placed, is inputted, whereas the count values of two counting blocks 239A and 239B are inputted in the photon incidence rate decision circuit 390A in the present modified example.

The switch SW11 is arranged in series with the output from the high-pass filter 272 in the counting block 239A, and the switch SW151 are arranged between the high-pass filter 272 of the counting block 239A and the voltage comparators 273 in the counting block 239B. Control signals SIG from the photon incidence rate decision circuit 390A control the switches SW11 and SW151, and when the control signal SIG is high level (H), SW11 is closed (ON) and SW151 is open (OFF).

There will now be described the operation of the counting block in the configuration as described above. The photon incidence rate decision circuit 390A evaluates the photon incidence rate according to the count value, and when the photon incidence rate is high, the control signal SIG is set to H, and then the switch SW11 is closed, along with opening the switch SW151. At this time, the counter redundant-operation circuit 391 of the counting block 239A does not generate redundant pulses due to the control signal SIG from the photon incidence rate decision circuit 390A. In other words, the photon counting blocks 239A and 239B count the current pulses respectively from the current input pins PIN11 and PIN21.

On the other hand, when the photon incidence rate is low, the photon incidence rate decision circuit 390A sets the control signal SIG to L, and opens the switch SW11, along with closing the switch SW. According to this control, the counter redundant-operation circuits 391 of the counting block 239A are activated, and generate redundant pulses. The period of the redundant operation of the counter and a degree of the redundant operation may be changed as appropriate according to the photon incidence rate. The additional heat amount control may be performed in a measurement-view basis, or at intervals shorter than the time constant of the temperature change in the system for managing temperature. Alternatively, the interval for the heat amount control may be extended as appropriate for the detector placed in a region where variation in the photon count rate is small.

In the counting block 239A, when such redundant operation as described above is performed, the input from the current input pin PIN11 of the counting block 239A does not enter the voltage comparators 273 of the counting block 239A, but the input enters the voltage comparators 273 of the counting block 239B. Accordingly, the current pulses from the current input pins PIN11 and PIN21 are counted collectively in the photon counting block 239B. The photon counting block 239A constantly keeps the redundant operation in the counter, thereby generating additional power consumption. Counting is not performed in the photon counting block 239A.

Since the counting result in the photon counting block 239A is not obtained during the period of the counter redundant operation, a result of counting in the photon counting block 239B is used to complement and generate the counting results in the photon counting blocks 239A and 239B. As a method for the complement, as described in the modified example of the second embodiment, a half of the counting result in the photon counting block 239B may be used as the estimate value of the counting result in each of the two photon counting blocks 239A and 239B. It is further possible to obtain a gradient of the number of incident photons from counting results of the surrounding pixels, and the counting result of the photon counting block 239B is divided proportionally based on the gradient, to obtain estimate values of the counting results in the photon counting blocks 239A and 239B.

According to the present modified example, the photon counting block for measuring the current pulse is separated from the photon counting block that performs the counter redundant operation, thereby producing an advantage that a circuit area can be used effectively. In this modified example, the ratio between the photon counting block for performing photon counting and the photon counting block for performing the counter redundant operation is set to one-to-one, but this ratio may be changed as appropriate.

Fourth Embodiment

In any of the aforementioned embodiment, the heat amount compensator 25 is placed in the chip 23 itself, and in particular, there has been described the case where the heat amount compensator is implemented on the circuit substrate. In the present embodiment, the heat amount compensator is placed in any of the elements constituting the radiation detector, except the chip.

With reference to FIG. 16, there will be described the radiation detector relating to the present embodiment, taking as an example, the X-ray detector of the X-ray CT apparatus. In FIG. 16, elements identical to those as shown in FIG. 3A are labeled with the same reference symbols, and they will not be described redundantly.

Figure 16A:
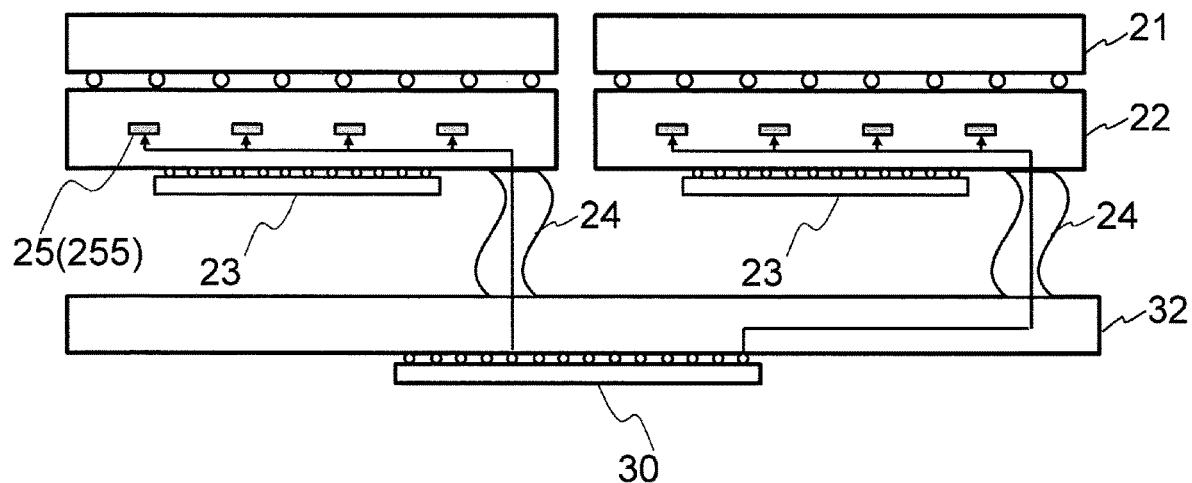
FIGS. 16A and 16B are conceptual diagrams showing detector elements relating to a fourth embodiment.

First, as shown in FIG. 16A, the modules 20 constituting the X-ray detector 2 are connected to the control circuit (FPGA) 30 for controlling the chips 23 via the cables 24. In the figure, only two modules 20 are shown, but the number of the modules may be two or more. In each module 20, the heating blocks 255 are placed within the substrate 22 that is equipped with the chip (LSI) 23. The heating block 255 may be, for example, the heating circuit employed in the first embodiment, or any element or material may be used for the heating block and there is no particular limit thereon as far as it is capable of controlling the amount of heat. The heating blocks 25 may be placed at positions in association with the photon counting blocks of the chip 23, or the heating blocks may be scattered at predetermined spacing. The heating blocks 255 are connected to the control circuit 30 via the cable 24.

The control circuit 30 controls the operation of the counting circuit 35, and also controls the amount of heat of the heating block 255. The method for the control is the same as the first embodiment, and for example, the control method modifies a resistance value, an applied voltage value, drive current, ON/OFF duty ratio, and others of the heating block 255, on the basis of the photon incidence rate, the amount of consumed current, temperature information, which are measured in the counting block 231.

Figure 16B:
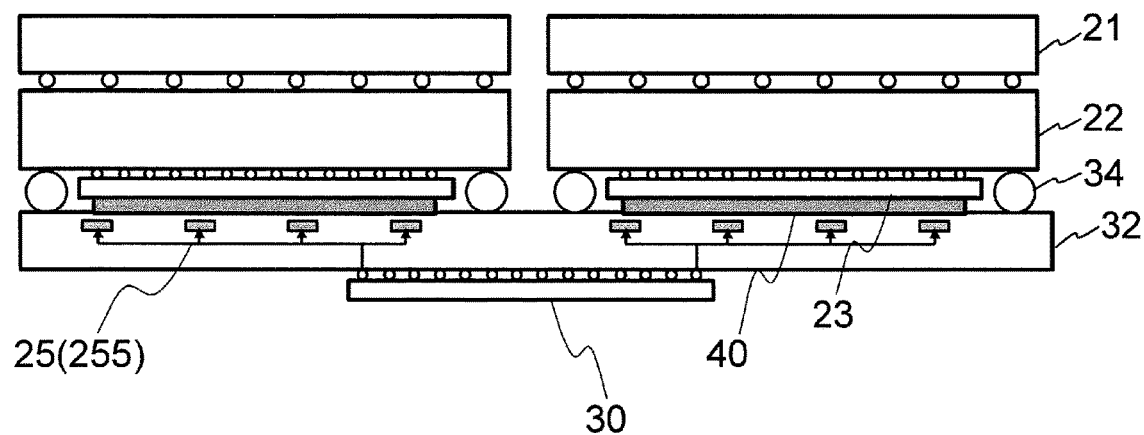

Next, in the configuration example as shown in FIG. 16B, the modules 20 are fixed on the substrate 32 that is equipped with the control circuit 30, and the heating blocks 255 are placed within the substrate 32. The control circuit may be configured by hardware such as FPGA, for instance. The chips 23 are electrically connected to the control circuit 30 via the connecting terminals 34. There are provided heat conduction sheets 40 in the space between the chips (LSI) 23 and the substrate 32, in order to transfer the heat generated from the heating blocks 255 to the chips 23. Also in this configuration example, the control of the heating blocks 255 by the control circuit 30, and its control method are the same as those in the aforementioned embodiments.

According to the present embodiment, the heating blocks 255 are placed outside the chip 23, and thus providing an advantage that the area of the chip 23 can be used effectively. There is also an advantage that the temperature control is achieved for the chip 23 not having the heat amount control function. In addition, since it is only required for the heating block 255 to keep the operation temperature constant in the chip 23, the heating block may be placed in any structure inside the X-ray detector 2, not only inside the chip 23 or on the substrate 32.

Fifth Embodiment

The present embodiment features that in a radiation detector where the plurality of detector elements is arranged, the heat amount compensators are provided in some of the detector elements. The present embodiment may be applied to all the aforementioned embodiments, and any of the configurations and methods as described in the aforementioned embodiments may be employed for the heat amount compensator and the control method thereof.

Figure 17:
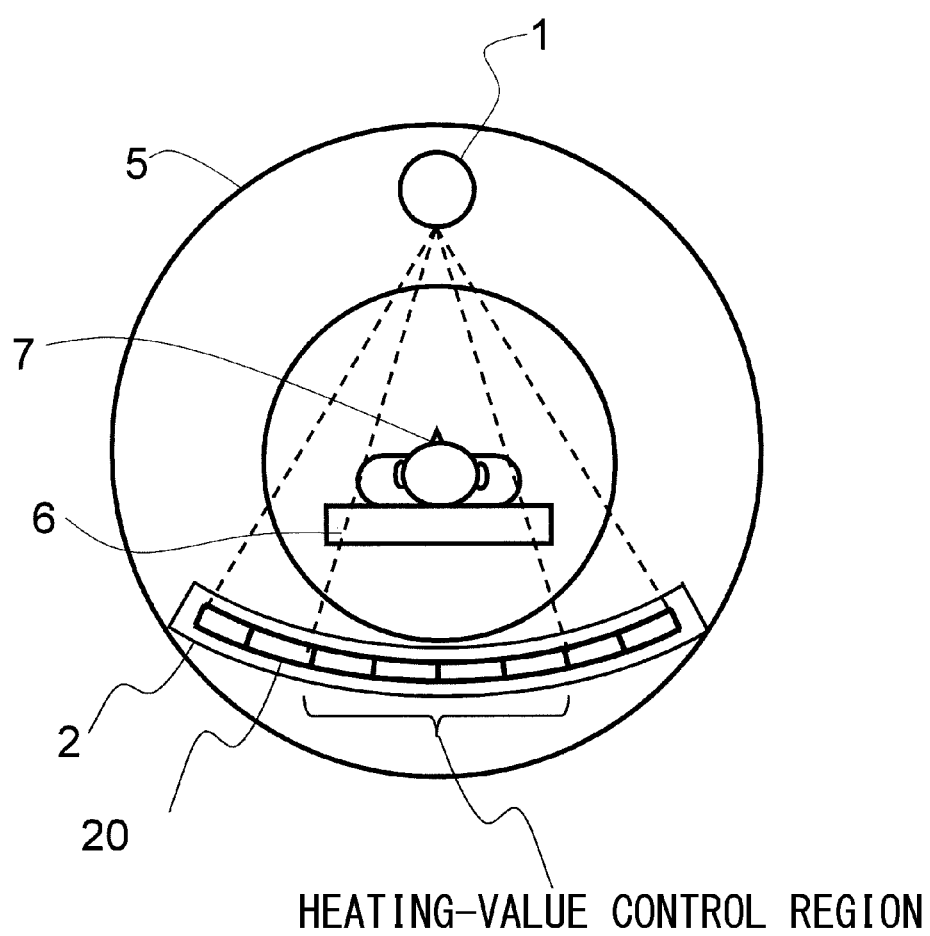
FIG. 17 illustrates the X-ray CT apparatus relating to a fifth embodiment.

There will now be described the radiographic imaging apparatus of the fifth embodiment, taking the X-ray CT apparatus as an example. In FIG. 17, elements identical to those as shown in FIG. 1 are labeled with the same reference symbols, and they will not be described redundantly. As shown in FIG. 17, the X-ray detector 2 is provided placing the X-ray source 1 at the center. The detection modules 20 provided somewhere around the center of the X-ray detector 2 are required to perform highly accurate detection, because the subject 7 is placed thereon. On the other hand, the detection modules 20 provided near the periphery of the X-ray detector 2 are not required to perform highly accurate detection, since the subject is not placed thereon. In view of this, only the detection modules 20 provided around the center (corresponding to a heat amount control region) where the subject is placed thereon, are set as a target region for the heat amount control, and the detection modules 20 placed near the periphery are set to be low in power consumption, and thereby reducing the power consumption in the X-ray detector 2.

In the present embodiment, the central part of the X-ray detector 2 is set as the heat amount control region, but the heat amount control region may be changed according to the size or layout of the subject 7. The embodiments of the present invention have been described so far, but the present invention is not limited to those embodiments. For example, elements not indispensable may be eliminated or added within the scope of the present invention. In the embodiments, there has been described the case where the means mainly performing control of the amount of heat is implemented by hardware provided on LSI or other similar element, but the present invention may also embrace software implementation.

DESCRIPTION OF SYMBOLS

1: X-ray source, 2: X-ray detector, 3: signal processor, 4: image generator, 20: detection module, 21: semiconductor layer, 23: chip, 35: photon-counting circuit, 230: output block, 231, 235, 237, 239: photon counting block, 25: heat amount compensator, 250: heating control block, 251, 255: heating block, 253: decoding circuit, 271: charge amplifier, 272: high-pass filter, 273: voltage comparator, 274: counter, 290: pseudo pulse generator, 390: photon incidence rate decision circuit, 391: counter redundant-operation circuit

What is claimed is:

1. A radiographic imaging apparatus comprising,
a radiation source and
a photon-counting detector configured to detect radiation emitted from the radiation source and to output electrical signals in association with the number of photons of the radiation, and further comprising,
a photon-counting circuit configured to count the number of the photons, and
a heat amount compensator configured to control an amount of heat of the photon-counting circuit according to detection of the number of photons, so as to provide the amount of heat independent of the number of photons being counted.

2. The radiographic imaging apparatus according to claim 1, wherein, the heat amount compensator controls the amount of heat, on the basis of a previously-obtained relation between a photon count rate and the amount of heat of the photon-counting circuit.

3. The radiographic imaging apparatus according to claim 1, wherein,
the heat amount compensator includes a heating element, and
the heat amount compensator controls the heating element according to an output from the photon-counting circuit.

4. The radiographic imaging apparatus according to claim 3, wherein,
the photon-counting circuit incorporates a plurality of circuit components, and
the heating elements are placed in proximity to the plurality of circuit components.

5. The radiographic imaging apparatus according to claim 3, wherein,
the heat amount compensator is placed in any of structural components constituting the photon-counting detector.

6. The radiographic imaging apparatus according to claim 3, wherein,
the photon-counting detector includes the photon-counting circuits more than one, and
the heating elements are placed between the photon-counting circuits being adjacent, among the photon-counting circuits.

7. The radiographic imaging apparatus according to claim 3, wherein,
the photon-counting detector comprises a semiconductor layer configured to detect radiation photons, and a substrate configured to support the semiconductor layer and to connect the semiconductor layer with the photon-counting circuit, and
the heating elements are placed within the substrate.

8. The radiographic imaging apparatus according to claim 3, wherein,
the photon-counting detector comprises,
the photon-counting circuits more than one,
a control circuit configured to control the photon-counting circuits, and
a substrate configured to support the control circuit and to connect the photon-counting circuits with the control circuit, and
the heating elements are placed within the substrate.

9. The radiographic imaging apparatus according to claim 1, wherein,
the heat amount compensator comprises a pseudo pulse generator configured to output a pseudo pulse to the photon-counting circuit, wherein,
the pseudo pulse generator controls at least one of a magnitude of the pseudo pulse and a generation period thereof, by using an output from the photon-counting circuit.

10. The radiographic imaging apparatus according to claim 9, wherein,
the photon-counting detector comprises the photon-counting circuits more than one, and
the pseudo pulse generator is placed in each of the photon-counting circuits.

11. The radiographic imaging apparatus according to claim 1, wherein,
the heat amount compensator corresponds to a counter redundant-operation circuit configured to generate (N+M) high-level signals and N low-level signal, with respect to the number of photons M being counted, where M is equal to 1 or 0, and N is an integer equal to or larger than 1.

12. The radiographic imaging apparatus according to claim 11, wherein,
the photon-counting detector comprises the photon-counting circuits more than one,
the photon-counting circuits are respectively provided with a plurality of counters having different thresholds for the photons being counted, and
at least one of the counters is provided with the counter redundant-operation circuit.

13. The radiographic imaging apparatus according to claim 9, wherein,
the photon-counting detector comprises the photon-counting circuits more than one, and
the heat amount compensator is placed only in one of the photon-counting circuits adjacent to each other, among the photon-counting circuits.

14. The radiographic imaging apparatus according to claim 13, wherein,
an output from the photon-counting circuit where the heat amount compensator is placed, among the adjacent photon-counting circuits in the photon-counting detector, is complemented by using an output from the photon-counting circuit where the heat amount compensator is not placed.

15. The radiographic imaging apparatus according claim 1, wherein,
the radiographic imaging apparatus is an X-ray CT apparatus.

16. The radiographic imaging apparatus according to claim 15, wherein,
the photon-counting detector is provided in a rotatable manner at a position opposed to the radiation source, placing the center of rotation therebetween, comprising the photon-counting circuits more than one being arranged in the direction of rotation, and the heat amount compensators are placed in some of the photon-counting circuits, arranged in a region including the center or in proximity to the center of the direction of rotation, among the photon-counting circuits arranged in the direction of rotation.

\* \* \* \* \*